US006985078B2

(12) United States Patent
Suzuki et al.

(10) Patent No.: US 6,985,078 B2
(45) Date of Patent: Jan. 10, 2006

(54) WEARABLE LIFE SUPPORT APPARATUS AND METHOD

(75) Inventors: Takuji Suzuki, Kanagawa-ken (JP); Miwako Doi, Kanagawa-ken (JP); Kazushige Ouchi, Tokyo (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 295 days.

(21) Appl. No.: 10/391,594

(22) Filed: Mar. 20, 2003

(65) Prior Publication Data

US 2003/0181795 A1 Sep. 25, 2003

Related U.S. Application Data

(63) Continuation of application No. 09/803,916, filed on Mar. 13, 2001, now Pat. No. 6,569,094.

(30) Foreign Application Priority Data

Mar. 14, 2000 (JP) ........................... P2000-069823
Oct. 30, 2000 (JP) ........................... P2000-329915

(51) Int. Cl.
*G08B 1/08* (2006.01)
*H04Q 7/00* (2006.01)
(52) U.S. Cl. ..................... 340/539.12; 340/573.1; 600/300; 600/301; 600/539
(58) Field of Classification Search ........... 340/539.12, 340/573.1; 600/300, 301, 539
See application file for complete search history.

(56) References Cited

U.S. PATENT DOCUMENTS

| 5,348,008 | A | | 9/1994 | Bornn et al. |
|---|---|---|---|---|
| 5,518,001 | A | | 5/1996 | Snell |
| 5,722,418 | A | | 3/1998 | Bro |
| 5,959,529 | A | * | 9/1999 | Kail, IV ................ 340/539.12 |
| 6,033,344 | A | | 3/2000 | Trulaske et al. |
| 6,083,156 | A | * | 7/2000 | Lisiecki ...................... 600/301 |
| 6,198,394 | B1 | * | 3/2001 | Jacobsen et al. ......... 340/573.1 |
| 6,241,684 | B1 | | 6/2001 | Amano et al. |
| 6,409,661 | B1 | * | 6/2002 | Murphy ...................... 600/300 |
| 6,416,471 | B1 | * | 7/2002 | Kumar et al. ............... 600/300 |
| 6,464,618 | B1 | | 10/2002 | Shea |
| 6,579,231 | B1 | * | 6/2003 | Phipps ....................... 600/300 |
| 6,602,191 | B2 | * | 8/2003 | Quy ........................... 600/300 |
| 2002/0019584 | A1 | * | 2/2002 | Schulze et al. ............. 600/300 |

FOREIGN PATENT DOCUMENTS

| EP | 0 846 440 | 6/1998 |
|---|---|---|
| JP | 9-322882 | 12/1997 |
| JP | 10-295651 | 11/1998 |
| JP | 10-305016 | 11/1998 |
| JP | 11-53319 | 2/1999 |
| JP | 11-53454 | 2/1999 |
| WO | WO98/38909 | 9/1998 |

* cited by examiner

*Primary Examiner*—Daniel Wu
*Assistant Examiner*—Samuel J. Walk
(74) *Attorney, Agent, or Firm*—Finnegan, Henderson, Farabow, Garrett & Dunner, L.L.P.

(57) ABSTRACT

A wearable life support apparatus worn by a user is disclosed. A physiological information acquirement unit acquires the user's physiological information. An action information acquirement unit acquires the user's action information. A status recognition unit recognizes the user's status in accordance with the action information. A physiological information decision unit decides whether the physiological information is normal in accordance with the user's status. A presentation unit presents the decision result of the physiological information decision unit to the user.

20 Claims, 25 Drawing Sheets

| | SLEEP | MEAL | COMMUTE | WORK | REST | READING | EXERCISE | ... |
|---|---|---|---|---|---|---|---|---|
| LYING | ○ | △ | × | × | | | | ... |
| SITTING | △ | ○ | △ | ○ | | | | ... |
| STANDING | × | △ | △ | △ | | | | ... |
| WALKING | × | × | △ | △ | | | | ... |
| RUNNING | × | △ | △ | △ | | | | ... |
| BICYCLE | △ | △ | △ | △ | | | | ... |
| MOTOR CAR | △ | △ | △ | △ | | | | ... |
| TRAIN | △ | △ | △ | △ | | | | ... |
| ... | ... | ... | ... | ... | ... | ... | ... | ... |

FIG.6

MONTHLY STRESS CALENDAR

SUZUKI, TAKUJI    OCT. 2000

| SUN | MON | TUE | WED | THU | FRI | SAT |
|---|---|---|---|---|---|---|
| 1 | 2 | 3 | 4 | 5 | 6 | 7 |
| 8 | 9 | 10 HIGH STRESS DETAIL | 11 HIGH STRESS DETAIL | 12 | 13 | 14 |
| 15 | 16 | 17 | 18 | 19 | 20 | 21 |
| 22 | 23 | 24 | 25 | 26 | 27 | 28 |
| 29 | 30 | 31 | | | | |

WEEKLY CALENDAR
1 2 3 4 5 6 7 8 9 10 11 12

- ROOT
  - LIFE WARE
    - STRESS
      - MONTHLY CALENDAR (MENTAL FATIGUE)
      - WEEKLY CALENDAR
      - LIST (TODAY)
      - DETAIL DISPLAY (TODAY)
    - CONCENTRATION
    - SLEEPINESS
    - OTHER

FIG.14

PHYSIOLOGICAL INFORMATION CORPUS

| DATE | TIME | ACTION | POSTURE/PITCH | PLACE | PULSE RATE | BLOOD PRESSURE | TEMPERATURE | GSR CHANGE |
|---|---|---|---|---|---|---|---|---|
| 2000/1/5 | 10:35 | WATCH TV | LYING | HOUSE | 70 | 130 | 36.0 | No |
| 2000/1/5 | 10:48 | WATCH TV | LYING | HOUSE | 120 | 130 | 36.0 | Yes |
| 2000/1/5 | 10:55 | WATCH TV | SITTING | HOUSE | 75 | 120 | 36.5 | No |
| 2000/1/5 | 11:02 | WALK | 80-100 | HOUSE→STATION | 120 | 143 | 36.7 | No |
| 2000/1/5 | 15:03 | WORK | SITTING | OFFICE | 133 | 150 | 36.9 | Yes |
| . | . | . | . | . | . | . | . | . |
| 2000/3/5 | 14:55 | RUN | 130-150 | STATION→COMPANY | 180 | 150 | 37.3 | Yes |

FIG.15A

PHYSIOLOGICAL INFORMATION CORPUS (AVERAGE VALUE)

| ACTION | POSTURE/PITCH | MONTH | TIME | PLACE | AVERAGE VALUE | | | |
|---|---|---|---|---|---|---|---|---|
| | | | | | PULSE RATE | BLOOD PRESSURE | TEMPERATURE | GSR |
| WATCH TV | LYING | 1 | 10:00-11:00 | HOUSE | 70 | 130 | 36.0 | No |
| WALK | 80-100 | 1 | 10:00-12:00 | HOUSE→ A STATION | 120 | 143 | 36.7 | No |
| RUN | 130-150 | 3 | 16:00-18:00 | B STATION→ C COMPANY | | | | Yes |
| SLEEP | LYING | 2 | 00:00-12:00 | HOUSE | | | | |
| MEAL | SITTING | 5 | 12:00-14:00 | | | | | |

FIG.15B

PHYSIOLOGICAL INFORMATION CORPUS (ONE DAY TREND)

| DATA TYPE | ACTION | MONTH | TIME | PLACE | TREND |
|---|---|---|---|---|---|
| NUMBER OF VEIN | WATCH TV | 1 | 10:00-11:00 | HOUSE | DATA |
| | | 1 | 11:00-12:00 | HOUSE | DATA |
| | | 1 | 12:00-12:30 | HOUSE | DATA |
| BLOOD PRESSURE | | | | | |

FIG.15C

PHYSIOLOGICAL INFORMATION CORPUS (ONE YEAR TREND)

| DATA TYPE | ACTION | MONTH | TIME | PLACE | TREND |
|---|---|---|---|---|---|
| NUMBER OF PULSE RATE | WATCH TV | 1 | 10:00-11:00 | HOUSE | DATA |
| | | 1 | 11:00-12:00 | HOUSE | DATA |
| | | 1 | 12:00-12:30 | HOUSE | DATA |
| BLOOD PRESSURE | | | | | |

FIG.15D

```
<?xml version="1,0" encoding ="Shift_JIS"?>
<mmdi>
    <body>
        <par>
            <acceleration src="AC000929202302.lwa" begin= "0.0s" dur= "243s" />
            <action- postue src="AP000929202302.lwa" begin= "0.0s" dur= "243s" />
            <pulse- wave src="PW000929202302.lwa" begin= "0.0s" dur= "243s" />
            <pulse- rate src="PR000929202302.lwa" begin= "0.0s" dur= "243s" />
            <img src="SP000929202302.lwa" begin= "0.0s" dur= "243s" />
            <audio src="SC000929202302.wav" begin= "0.0s" dur= "243s" />
        </par>
    </body>
    <recg>
        xmlns:rdf="http://www.w3c.org/1999/02/22-rdf-syntex-nsw"
        xmlns.LW="http://description.toshiba.cp.jp/LifeWare_lw"
        xmlns.LWPAR="http//description.toshiba.cp.jp/LifeWare_lw"
        : <rdf:Desctiption about="AP000929202302.lwa">
            <LW:action_recg rdf:resource="AC000929202302.lwa">
        <rdf:Desctiption >
        <rdf:Desctiption about ="PR000929202302.lwa">
            <LW:p-p_period rdf:resource="PW000929202302.lwa">
        <rdf:Desctiption >
    </recg>
</mmdi>
```

FIG.16

```xml
<?xml version="1,0" encoding ="Shift_JIS"?>
<lwml>
    <head>
        <sensor-module> 0001 </sensor-module>
        <sensor-position> lumbar </sensor-position>
        <data-type> acceleration </data-type>
        <dimensions> 2 </dimensions>
        <sampling- rate> 0.05 </sampling- rate>
        <date> 2000-9-29T20:23:07 </date>
        <unit-x> s </unit-x>
        <unit-y> G </unit-y>
        </label>
            <itemname> Acceleration-X </itemname>
            <itemname> Acceleration-Y </itemname>
            <label>
    <head>

<body>
    <items>
        <item type= "stream">
-0.09521484375          0.07568359375
-0.09521484375          0.07568359375
-0.09521484375          0.07080078125
-0.09521484375          0.0732421875
-0.09521484375          0.0732421875
-0.09521484375          0.068359375
-0.09521484375          0.07080078125
      ⋮                      ⋮
        </items>
    </items>
</body>
</lwml>
```

FIG.17

| | PULSE RATE | | | BLOOD PRESSURE | | | TEMPERATURE |
|---|---|---|---|---|---|---|---|
| | TODAY | PAST 1W | PAST 1M | TODAY | PAST 1W | PAST 1M | TODAY |
| WORK (DESK WORK) | 81.2 | 78.1 | 79.7 | 131/78 | 128/61 | 126/74 | |
| WORK (GO OUT) | 121.3 | 102.1 | 113.1 | | | | |
| WORK (MEETING) | 120.1 | 90.1 | 89.2 | | | | |
| COMMUTING (TRAIN) | | | | | | | |
| COMMUTING (WALKING) | | | | | | | |
| COMMUTING (RUNNING) | | | | | | | |
| SLEEPING | | | | | | | |
| TAKING A MEAL | | | | | | | |

HEALTH CONDITION OF TODAY

Your health condition is····.

CONCLUSION : NO PROBLEM
STRESS : A LITTLE HIGH

MOVEMENT QUANTITY VS. ABSORBED CALORIE
A LITTLE SHORTAGE OF EXERCISE (500 kcal)

SLEEP TIME : A LITTLE SHORTAGE
(5 HOURS AT LAST NIGHT)

ACTION IN HOUSE

FIG.18

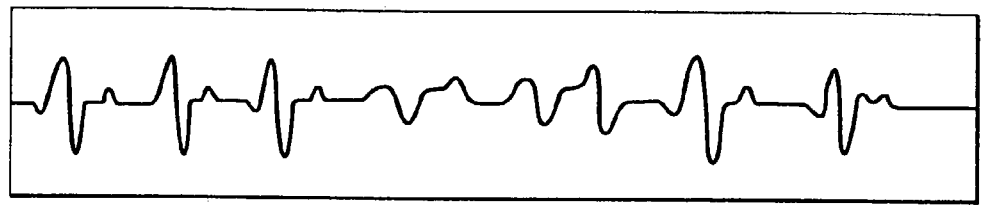
FIG.23
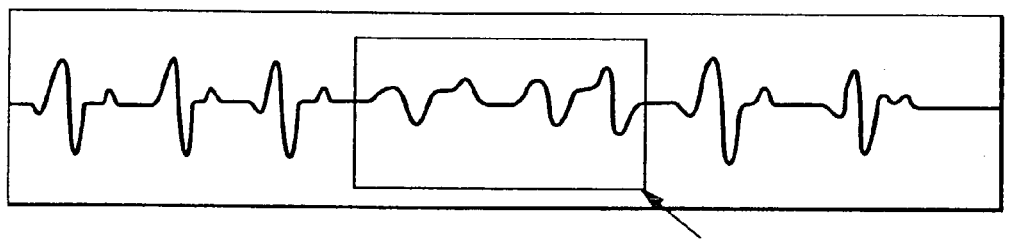
FIG.24
1. 2000/06/23 21:24:35   NO PROBLEM → TO DETAIL DATA
2. 2000/02/14 22:00:03   FIT AFTER 10 MINUTES → TO DETAIL DATA
3. 1999/11/11 19:31:42   NO PROBLEM → TO DETAIL DATA
FIG.25

WEARABLE LIFE SUPPORT APPARATUS AND METHOD

This is a continuation of application Ser. No. 09/803,916, filed Mar. 13, 2001 now U.S. Pat. No. 6,569,094, which is incorporated herein by reference.

FIELD OF THE INVENTION

The present invention relates to wearable life support apparatus and method for measuring a user's status while wearing the device and for supporting the user's activities such as health control and personal navigation.

BACKGROUND OF THE INVENTION

Geriatric diseases such as an apoplexy, heart disease, and diabetes, may originate because of life style choices such as an unbalanced diet, lack of exercise, an irregular life, and stress. Such diseases are thus defined as "life style related disease". Recently, the disease due to the life style is greatly recognized. Especially, the recognition advances along direction to make much of first prevention (health) from usual second prevention (an early detection, an early medical treatment).

Many apparatus of a wearable type have been suggested to acquire the user's physiological information and control the user's health condition. For example, in Japanese Patent Disclosure (Kokai) PH11-53319, the user inputs meal data and movement data through a portable terminal, or the sensor measures these data. The user's health is then controlled based on the data. In Japanese Patent Disclosure (Kokai) PH10-295651, a host computer controls health information of the user through a network. However, in these references, the user must input meal menu or meal material as the food data, and this operation is very troublesome for the user. In addition to three times meal every day, it is very hard for the user to input something between meals and his luxury meals.

In Japanese Patent Disclosure (Kokai) PH11-53454, the portable terminal presents health advice to the user at random. Because the user often forgets health control if he does not always take care of health. However, in this reference, the health advice is presented to the user at random. It is useless if the health advice is not present at adequate timing based on the user's status. Conversely, it disturbs the user's work and the user is put under stress.

In Japanese Patent Disclosure (Kokai) PH9-322882, a portable terminal of a wearable type records the health information. In this case, by setting times to record vital data, the health information is output by speech. However, in this reference, the measurement time is presented, but the user must operate the measurement. Furthermore, the user cannot understand the relationship with his behavior and the reason of change of health condition. When the record time is presented to the user, if the user cannot keep quiet, he feels inconvenience in practical use.

Wearable computers have been suggested. The wearable computer is divided into each component (ex. CPU, display, communication part) worn by the user. A physiological sensor and an environmental sensor are combined with the wearable computer. By recognizing the user's status, adequate information is presented to the user. This function to recognize the user's status is called "context awareness". This operation is executed by speech dialogue because of hand-free operation.

Furthermore, in Japanese Patent Disclosure (Kokai) PH10-305016, the user's action information is acquired by location information from a GPS (Global Positioning System), schedule data, and the physiological information such as brain waves. The action information is recorded in correspondence with the physiological information such as pulse rate, body temperature, blood pressure, sweating. In this case, decision data representing whether the schedule is good for the user is also recorded, and advice of future schedule is created based on the decision data. However, in this reference, because the user must previously input all schedule information, this operation is very troublesome for the user and the action information is not sufficiently obtained. Furthermore, even if the user inputs his schedule, he does not always follow that schedule. In short, it is possible that his actual behavior is not matched with the schedule, and the schedule is incorrect.

As mentioned-above, many apparatuses of a wearable type to acquire the user's physiological information and control the user's health condition are known. However, the measured physiological information largely changes according to the user's behavior. Therefore, a correct decision of health condition is difficult if the physiological information is not measured in correspondence with the user's behavior.

SUMMARY OF THE INVENTION

It is an object of the present invention to provide a wearable life support apparatus and method for correctly supporting the user's life such as health control by a wearable device.

According to the present invention, there is provided a wearable life support apparatus which is worn by a user, comprising: a physiological information acquirement unit configured to acquire physiological information; an action information acquirement unit configured to acquire action information; a status recognition unit configured to recognize a status in accordance with the action information; a physiological information decision unit configured to decide whether the acquired physiological information is normal in accordance with the recognized status; and a presentation unit configured to present a decision result of said physiological information decision unit.

Further in accordance with the present invention, there is also provided a method for supporting a user's life using a wearable type device, comprising the steps of: acquiring the user's physiological information through the wearable type device; acquiring the user's action information through the wearable type device; recognizing the user's status in accordance with the action information; deciding whether the physiological information is normal in accordance with the user's status; and presenting a decision result at the deciding step through the wearable type device.

Further in accordance with the present invention, there is also provided a computer-readable memory containing computer-readable instructions to support a user's life using a wearable type device, comprising: an instruction unit to acquire the user's physiological information through the wearable type device; an instruction unit to acquire the user's action information through the wearable type device; an instruction unit to recognize the user's status in accordance with the action information; an instruction unit to decide whether the physiological information is normal in accordance with the user's status; and an instruction unit to present the decision result through the wearable type device.

BRIEF DESCRIPTION OF THE DRAWINGS

FIG. 6 is a schematic diagram of a correspondence table between action information and behavior.

FIG. 14 is a display example of stress during one month.

FIGS. 15A–15D are examples of a memory format of various kinds of the physiological information corpus.

FIG. 16 is a display example of synchronization data of sensor information corpus.

FIG. 17 is a display example of sensor data of sensor information corpus.

FIG. 18 is an example summary of health conditions during one day shown on a portable display.

FIG. 23 is a display example of physiological information corpus.

FIG. 24 is a selection example of retrieval area of physiological information.

FIG. 25 is a display example of the retrieval result.

DETAILED DESCRIPTION OF THE PREFERRED EMBODIMENTS

Figure 1:
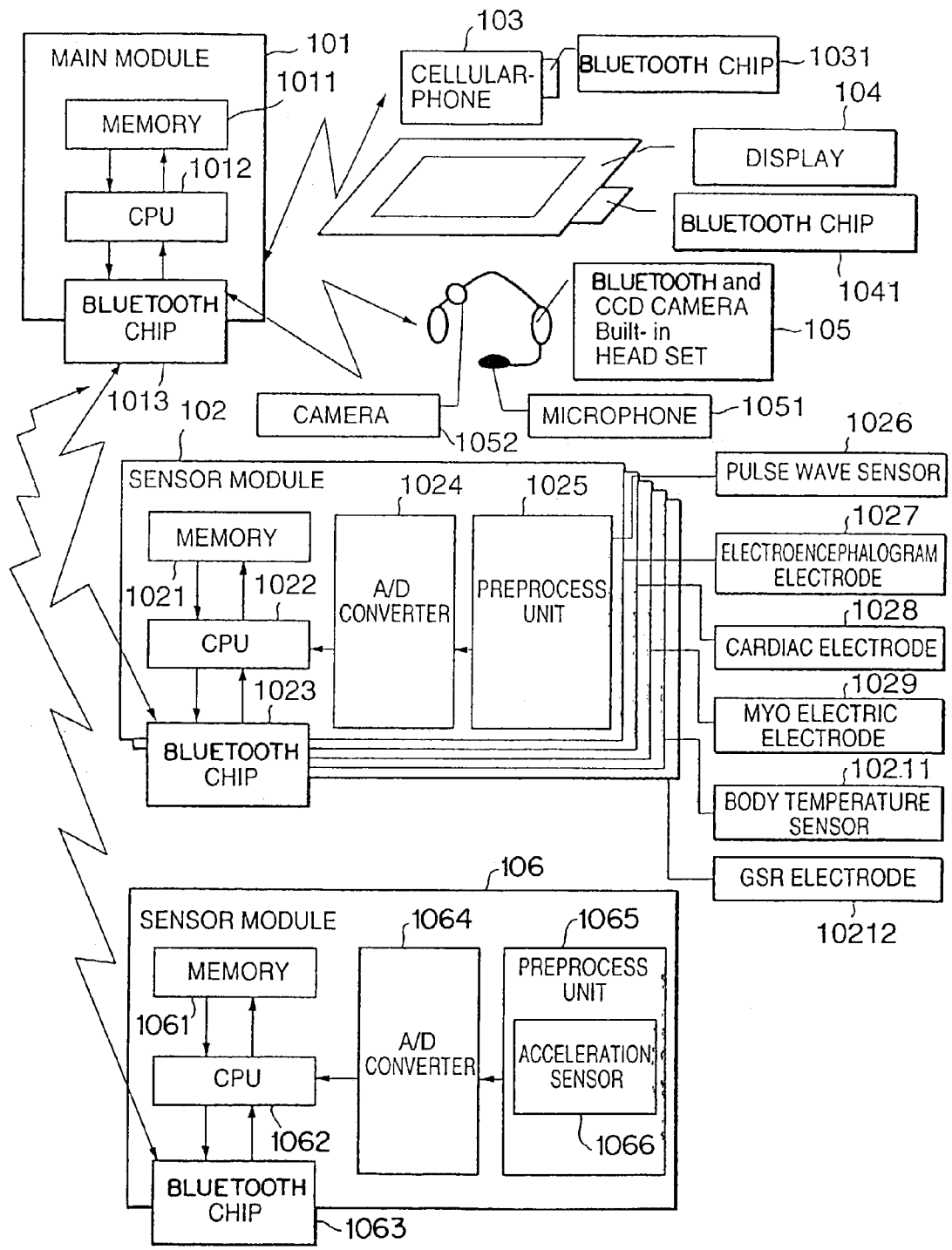
FIG. 1 is a block diagram of an embodiment of a wearable life support apparatus.

Hereinafter, embodiments of the present invention are explained with reference to the drawings. FIG. 1 is a block diagram of a wearable life support apparatus according to an embodiment of the present invention. In FIG. 1, a main module 101 includes a memory 1011, a CPU 1012, and a Bluetooth chip 1013 to communicate between modules. Bluetooth is one example of a short distance-wireless communication means; other wireless or wired communication protocols could also be used. The main module 101 executes data reservation for the system, unification processing of the system, data communication between modules, and communication to a home server and a management server.

Figure 2:
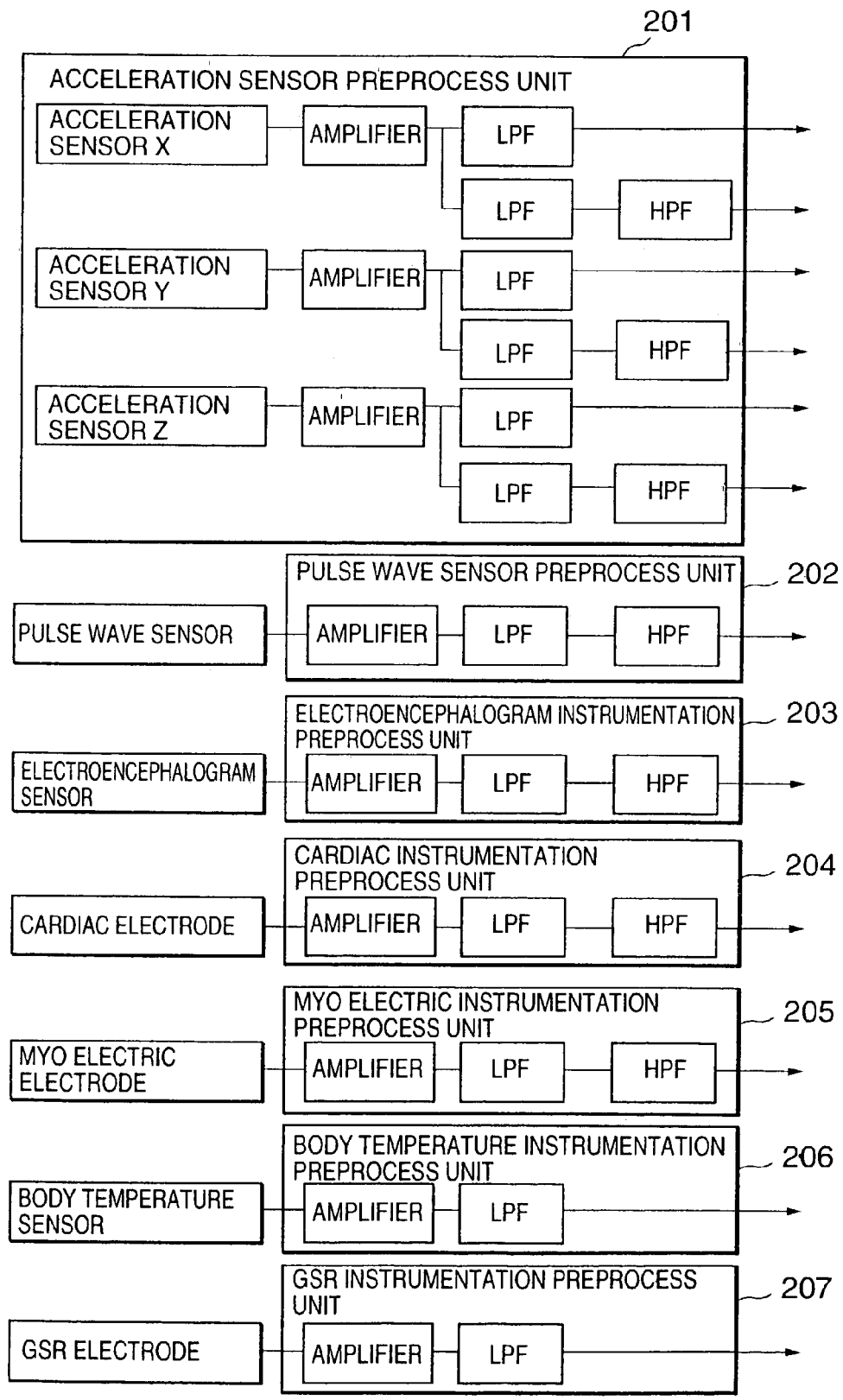
FIG. 2 is an example of components in a sensor module of the wearable life support apparatus shown in FIG. 1.
Figure 3:
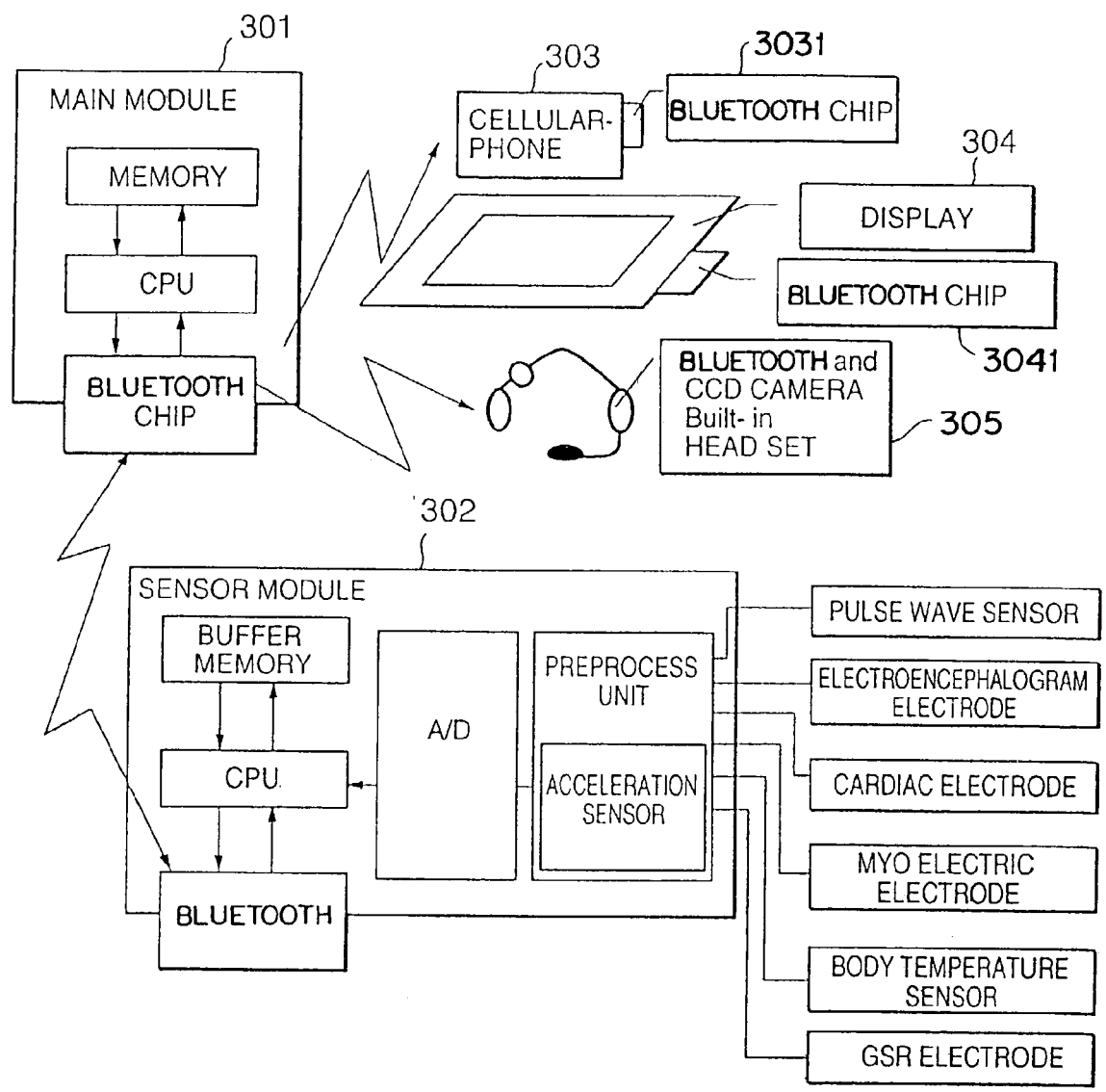
FIG. 3 is a block diagram of a wearable life support apparatus according to a modification of the embodiment.
Figure 4:
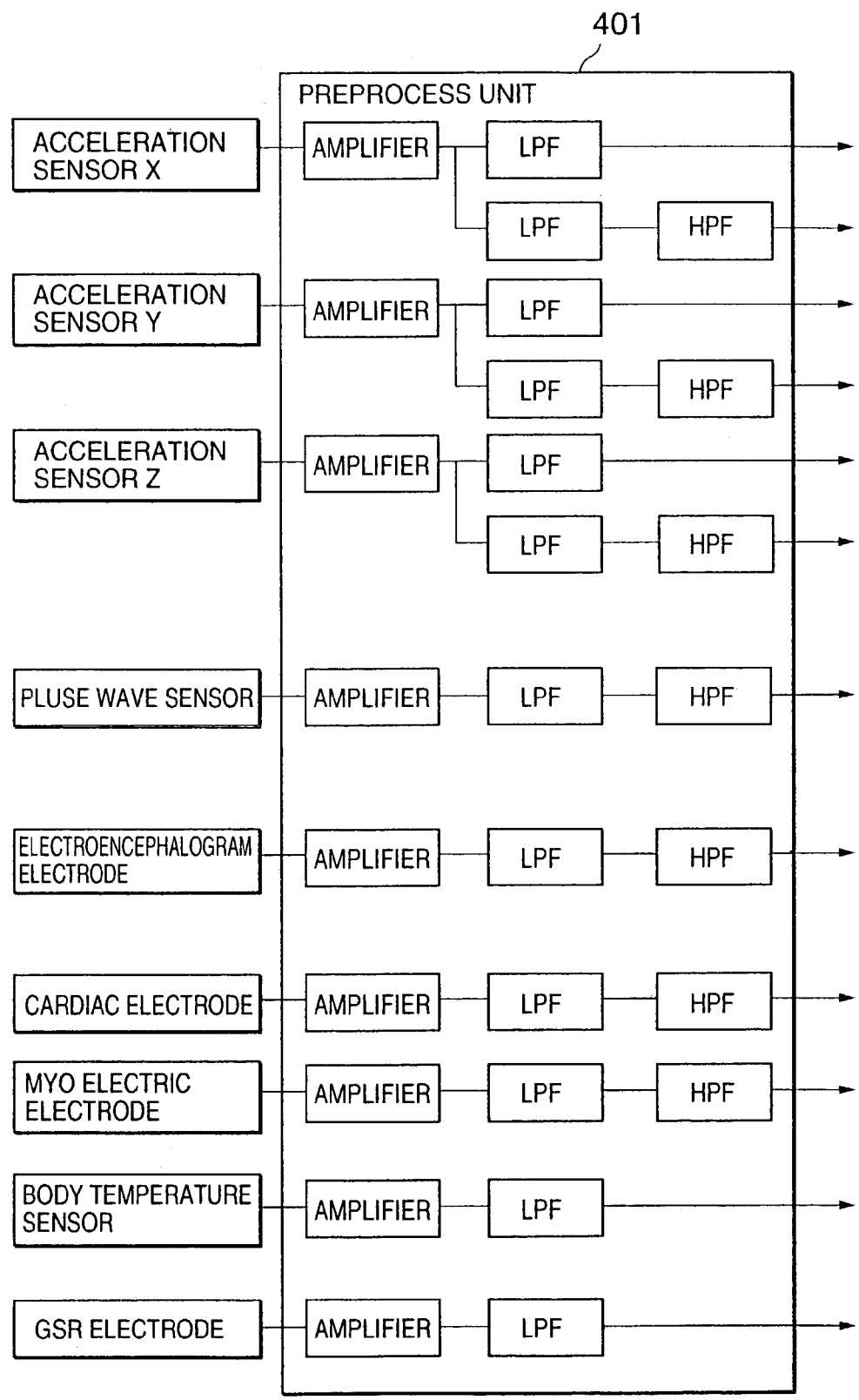
FIG. 4 is an example of components in a sensor module of the wearable life support apparatus shown in FIG. 3.

A sensor module 102 includes a memory 1021, a CPU 1022, a Bluetooth chip 1023, an A/D converter 1024, and a preprocess unit 1025. The preprocess unit 1025 executes amplification and preprocessing for signals from each sensor (pulse wave sensor 1026, electroencephalography electrode 1027, cardiac electrode 1028, myoelectric electrode 1029, body temperature sensor 10211, GSR electrode 10212). The Bluetooth chip 1023 executes data communication to the main module 101. In the same way, a sensor module 106 includes a memory 1061, a CPU 1062, a Bluetooth chip 1063, an A/D converter 1064, and a preprocess unit 1065. The preprocess unit 1065 includes an acceleration sensor 1066. In this case, as shown in FIG. 2, the preprocess unit 201 (1065) executes amplification and preprocessing for signals from each acceleration sensor X, Y, Z (1066). The preprocess unit 202-207 (1025) in each sensor module 102 is respectively connected to each sensor (1026-10212). However, as shown in FIGS. 3 and 4, one sensor module 302 including a preprocess unit 401 may be connected to all sensors as one body. If the sensor module is composed as one body, wiring must be formed from each sensor to the sensor module. Accordingly, as shown in FIGS. 1 and 2, it is desirable that the sensor module is dependently composed for each sensor and the wiring is omitted using Bluetooth. Furthermore, processing of the sensor and the module may be commonly executed. The CPU may be executed by utilizing a micro-controller for example, Micro Chip Technologies Co., PIC 16F877) including A/D conversion function, and another A/D converter may not be prepared. Each preprocess unit 1025 (202-207) and 1065 (201) amplifies by gain suitable for each signal and includes a high-pass filter or a low-pass filter in proportion to a band of the signal. If necessary, each sensor includes a plurality of channels.

A cellular-phone 103 (303) may be a common portable telephone including a liquid crystal display, operation buttons, and a communication unit to input/output speech. The cellular-phone 103 (303) includes a Bluetooth chip 1031 (3031) to communicate to the main module 101 (301). By this communication, input/output of speech and cursor control of cursor key is executed.

A display 104 (304) is a liquid crystal screen only, and controls the display content from the main module 101 (301) to Bluetooth chip 1041 (3041). A Bluetooth/CCD camera built into a head set 105 (305) is a device for speech/image interface, and stores Bluetooth chip to execute input/output of speech and acquirement of image. Both the cellular-phone 103 (303) and the headset 105 (305) can be utilized at the same time. Furthermore, a digital camera 1052 differently equipped on the headset 105 may input an image.

Figure 5:
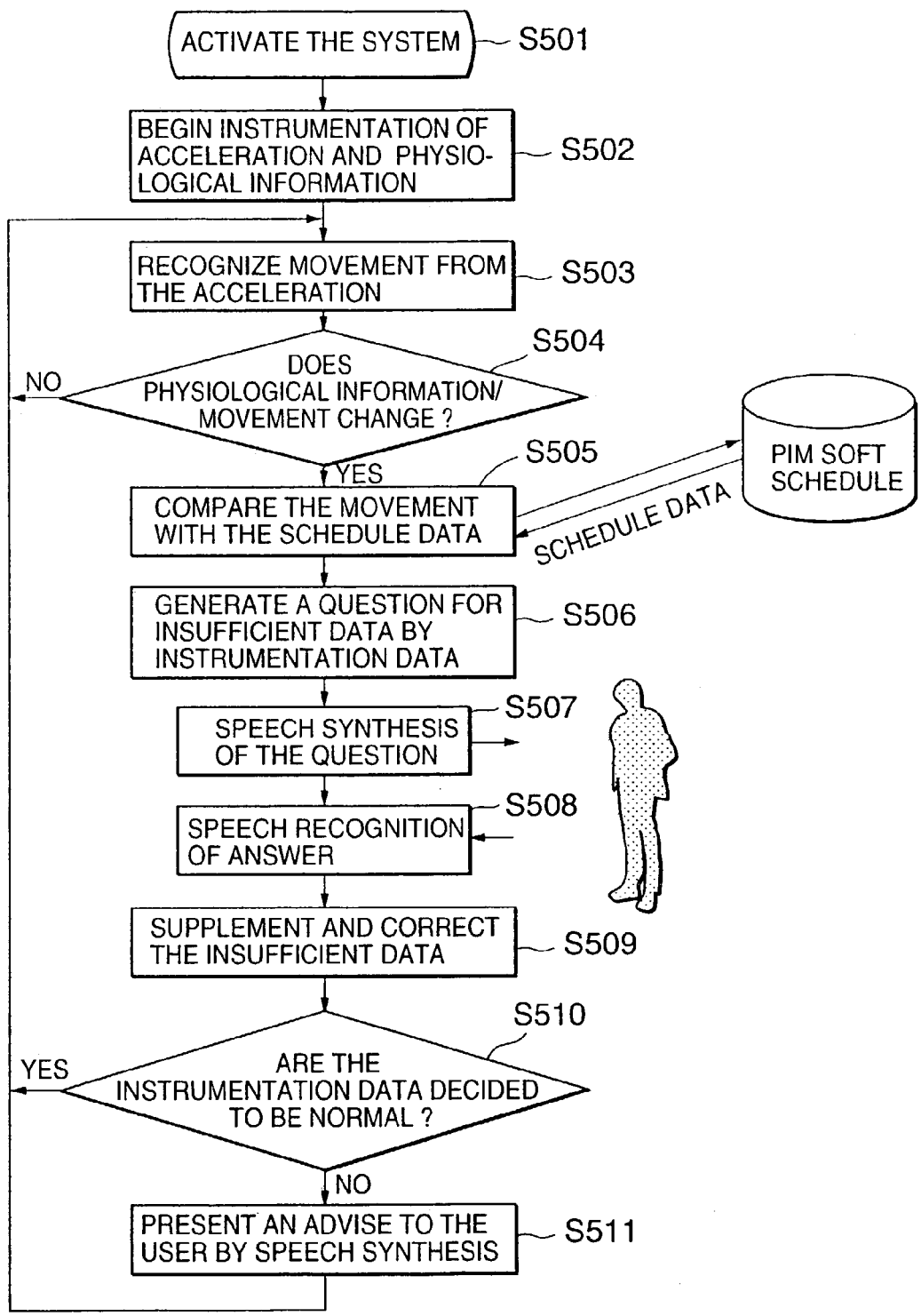
FIG. 5 is a flow chart of processing of the wearable life support apparatus according to the first embodiment of the present invention.

FIG. 5 is a flow chart of processing of the wearable life support apparatus according to the first embodiment. Assume that the user carries a wearable device including the main module 101, each sensor module 102 and 106, the cellular-phone 103, the display 104, and the headset 105. When the system is activated (S501), each sensor inputs some physiological information and acceleration sensor measures the acceleration (S502). An analogue signal from the sensor is processed as amplification, filtering, and A/D conversion by the sensor module. The A/D converted signal is transferred to the main module 101. The main module 101 processes the instrumentation data by preset logic, and decides the user's status.

First, the user's action (movement) is recognized by the acceleration information (S503). As the recognition method, for example, three-dimensional acceleration sensor is attached to predetermined part of the user's body in order to measure the action. In case of measuring motion of body-trunk-part, this sensor is attached to the waist. An inclination of the sensor is calculated from DC (direct current) element obtained by low-pass filter output of acceleration waveform, and the posture is detected. An action (ex. walking, running, riding a bicycle, riding an automobile, taking an electric train) is discriminated from a frequency element and change pattern of AC (alternating current). For example, as the acceleration sensor, a two-dimensional acceleration sensor (Analogue Devices Co., ADXL202JQC) is utilized. A three-dimensional acceleration sensor is composed by an orthogonal location of two-dimensional acceleration sensor.

In order to recognize the user's location, in case of being indoors, the main module communicates with a wireless tag (Bluetooth) in each room, and detects the user's location. In case of being outdoors, the user's location is detected, for example, using a position information service of the cellular-phone (PHS) or GPS. At the same time, the physiological information is measured. This measurement method is explained hereinafter.

In a pulse wave sensor 1026, a change in blood flow of a peripheral blood vessel such as the measurement part (finger, wrist, ear) is detected as a photoelectrical signal. An incandescent lamp or LED irradiates a light of absorption of wavelength of hemoglobin to the part gathering blood vessels, and a photodiode converts the transparent light or the reflected light to a photoelectrical signal. These instrumentation data are amplified and filtered by the preprocess unit and converted to a digital signal by an A/D converter. Then, the digital signal is transferred to the main module. The main module detects a peak interval of this instrumentation of electric potential waveform or analyzes the frequency and calculates a number of pulses (pulse rate) from this peak frequency.

Furthermore, the pulse wave sensor 1026 is located at a predetermined distance on the part of the user's body. Two waveforms are respectively measured, each digital signal is transferred to the main module, and the blood pressure or elastic rate of the blood pressure or elastic rate of the blood vessel may be calculated from the difference between the two waveforms. In case of measuring a pulse, by using an electrocardiogram, the number of beats may be calculated from the peak interval or the peak frequency obtained by frequency analysis. This pulse value and blood pressure value are continually measured and stored in the memory 1011 of the main module 101. As for the body temperature, the output of a thermometer is converted to temperature. Furthermore, output of GSR is also stored in the memory 1011 of the main module 101. In addition to this instrumentation value, analogue (voltage) data from the acceleration sensor 1066 are stored in the memory 1011 after A/D conversion. These data are mutually corresponded by adding the measurement time to each data or by storing each data in the same record.

While the measurement is continually executed, if the physiological information (pulse rate, blood pressure, body temperature) changes, or if the action information changes such as "walking stops", this change status is detected (S504). Then, the action information (the user's behavior) is compared with the user's schedule data (S505), and a question for insufficient data or contradiction point is presented to the user by speech synthesis (S506, S507). For example, when an absolute value along X, Y, Z axes directions of AC element from the acceleration sensor is above a threshold, the user is decided to be moving, a question "What are you doing?" is presented to the user, and the user's behavior information is input by speech-recognition of the user's reply (S508, S509). Furthermore, the behavior predicted from the acceleration data is compared with the schedule data of the present time. In case of non-coincidence, a dialogue to confirm the schedule item is presented to the user, and the prediction result is corrected according to the user's reply.

Conversely, if the user is decided to be not moving, this behavior is compared with the schedule of the present time to check whether non-moving behavior is correct. If the behavior does not match with the schedule, a question is presented to the user. For example, this inquiry is executed by speech dialogue. This processing is based on an experience rule to relate the action information with the behavior. For example, when the action information "walking" is acquired, combination between action "walking" and each behavior "sleeping", "watching TV", "watching movie" does not actually exist. Accordingly, the relationship of all combinations is previously stored in the memory. In this case, the behavior corresponding to the action information is retrieved from the memory, and the behavior is compared with the schedule of the present time.

FIG. 6 shows a table representing correspondences between the action information and the actual behavior. In FIG. 6, actual possibility of the action (lying, sitting, standing, and so on), while the user performs the behavior (sleep, meal, commute, and so on) is represented by "O" (The behavior is almost performed by the action.), "Δ" (The behavior is sometimes performed by the action), "X" (The behavior is not performed by the action). This probability may be represented by numerals (For example, 0~100).

For example, while the schedule shows a meeting in the meeting room of the company, if the action information is "continuous walking", the combination between "walking" and "meeting" is represented as "x" in the table. Accordingly, the question "The schedule represents meeting, but you are walking outside. How does your schedule change?" is presented to the user. When the user replies such as "I have to go out because of customer trouble.", the system changes the schedule of the present time as "treatment of trouble at a customer (go out)". In addition to the instrumentation and the dialogue, image of the user's meeting status (customer's image) may be input by CCD camera 1052 on the head set 105. At the same time, the microphone 1051 may record the dialogue between the user and the customer by directivity along the meeting direction. These data are mutually related by writing the same record time or the same file name.

Furthermore, if the recognized behavior of the present time should be performed before in the schedule, the user's behavior is delayed from the scheduled time. Accordingly, an inquiry message to change the remaining schedule for the day is presented to the user. For example, the inquiry "You are schedule to go out at 2:00 PM, but you did not go out. How do you change the schedule?" is output to the user.

The physiological information may be used for comparison with the schedule. For example, when the user's pulse is quick while working at a desk, it is possible that he changed the schedule. Accordingly, a question "Are you walking or running now?" is output to the user. If he is working at a desk, an increase in the pulse rate may be mentally or sickly caused. First, a question "Are you working hard now?" is output in order to confirm whether the user is under stress. If the user does not reply, the user is recognized to be in serious condition. In this case, the user's status is reported to a family doctor by the cellular-phone or a warning is given to those around the user.

Next, it is decided whether the physiological information corresponding to the action information (behavior) obtained from these results is normal (S510). As a decision method of normal/abnormal, a standard limit of the physiological information for each behavior is stored as a parameter in a memory of the main module, and the measured physiological information is compared with the standard limit. If it is within the standard limit, the user is decided to be normal. If it is over the standard limit, the user is decided to be abnormal. In case of abnormal, a message "You are walking to the customer's office now. Your pulse is high for walking. Do you feel well? You had better take a rest." is presented to the user by speech synthesis (S511). If the user accepts this message, he replies, for example, "all right (acceptance)", otherwise he may reply, for example, "Shut up! (refusal)". This reply is recognized in order to confirm whether the user accepts or rejects the message. If the user thinks that the standard limit (parameter) is strictly set, he replies "No problem" or "Shut up!". In this case, the, parameter is slightly corrected in order to loosely set.

Figure 7:
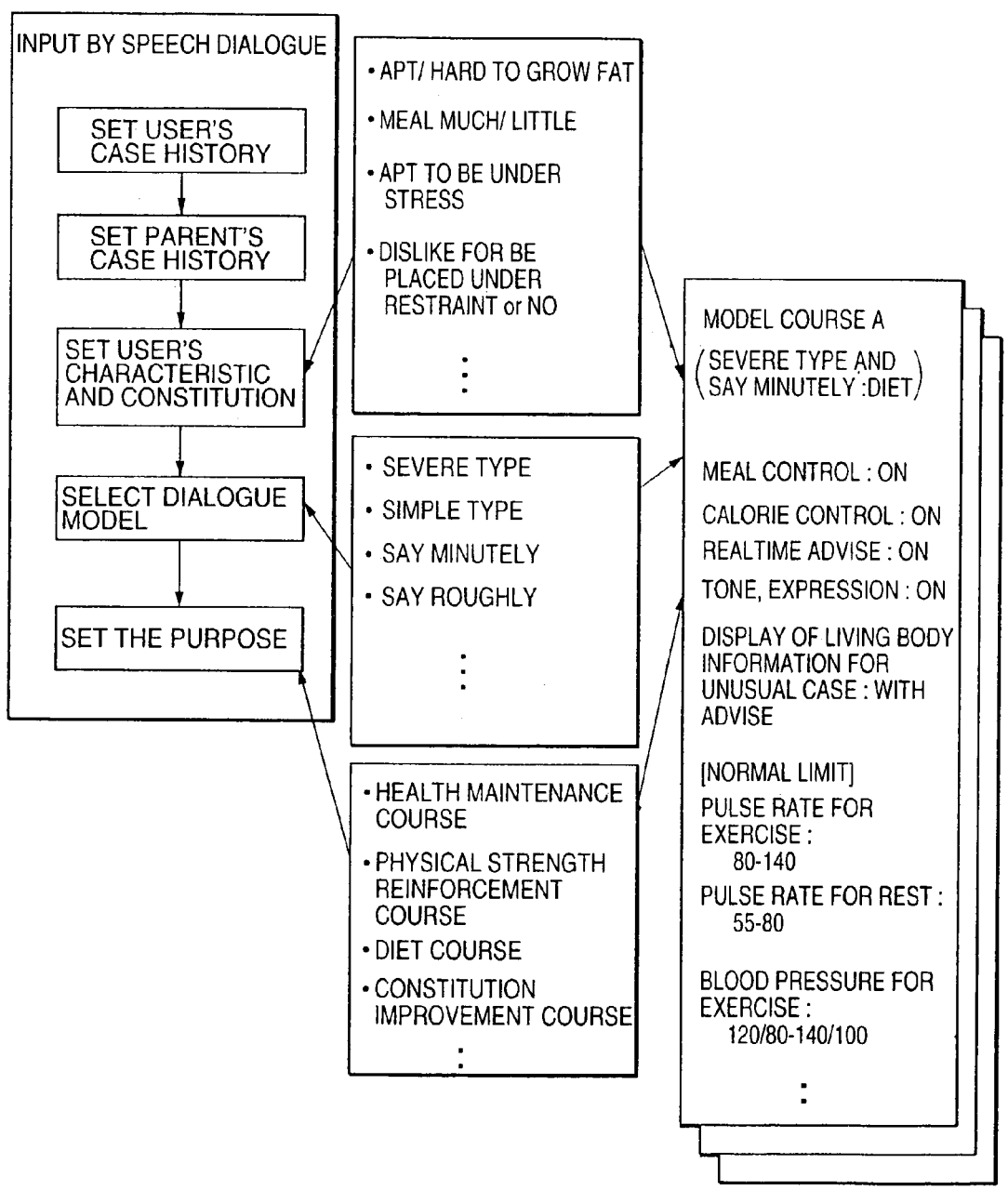
FIG. 7 is a schematic diagram of a relationship plan to set personal tendency and limit of measurement value.

The threshold limit to detect abnormal status is set as a parameter according to the user's purpose and personal information such as his constitution or heredity by set mode. FIG. 7 shows a relation between the threshold set and the screen. As shown in FIG. 7, when the user inputs each item in order by speech dialogue at operation start time, the threshold corresponding to each item is set, and the model course is selected by weighing of the constitution or the heredity. For example, in case the meal control is set "ON", a myoelectric sensor of chewing muscles is utilized to measure the movement of the jaw. In case the real time advice is set "ON", the decision result of the measurement and the advice are presented at that timing. Furthermore, when the pulse rate during exercise is above the threshold of exercise, a warning is presented.

As the presentation method, following several kinds are selectively set at the initialization mode. As a first method, the values measured by the wearable sensor are directly presented, such as "The upper blood pressure is 130 and the lower blood pressure is 70.". As a second method, the measurement value is compared with the standard value. If it is over the standard value, the message is presented, such as "The blood pressure value is over the standard value.". Furthermore, advice may be additionally presented, such as "Your blood pressure value is continuously high. You had better consult a doctor.". Furthermore, when the wearable sensor measures the abnormal value, the user's behavior is inquired, such as "Your blood pressure value is over the standard value. What are you doing? What have you been doing?". As a third method, the time (place, behavior) to measure the physiological information is set and the data change of every day is fed back to the user. For example, the body temperature thirty minutes after the user gets up is measured every morning. The data change such as "Your body temperature is higher than usual." is presented in order for the user to intuitively understand the status.

The utilization mode is explained for each life spot. During sleeping, the physiological information is only measured by small electric power mode. The message is not presented to the user except for serious case. As the small electric power mode, a battery is charged. In case of the hour of rising set by the schedule, the user wakes up because of a speech or alarm of vibration from the headset. The status that the user wakes up is detected by electroencephalography. If he awakes before alarming but does not rise yet, the message "It is the hour of rising" is presented instead of the alarm. A posture sensor such as the acceleration sensor detects the status that the user actually gets up. If the user does not rise yet, the message is presented again to urge the user to rise. Next, when the posture sensor detects the status that the user got up, the user is decided to start his action. Then, by referring to the schedule data, the leaving time from the house is informed to the user by counting backward from going time to the office. For example, the message "You had better leave the house at 8:10 AM." is output. Furthermore, a subtraction of the hour of rising from the hour of sleeping is calculated, and sleeping time is detected. If it is shorter than average sleeping time by over set limit, the message "Your sleeping time is short. You had better come back home early without overwork." is presented while he is going to the office. This message may be also presented to the user during overtime working.

As for the meal, the electromyogram of chewing muscles and the speech detects the status that the user takes a meal. An electrode set at the jaw measures the electromyogram of chewing muscles. If the electromyogram periodically repeats as the same change of period of chewing, the user is decided to be taking a meal, and a question "Are you eating?" is presented. When the user replies "Yes.", a question "What are you eating?" is presented. Alternatively, an object image of the meal is obtained and the dish is recognized by the image. In case of eating-out, components printed on a menu are recognized or the component is detected using a spoon or chopsticks including sensors. The quantity of food not consumed is inquired or input by image-recognition after the meal. The amount of chewing is counted based on the electromyogram of the chewing muscles, and a large or small amount of chewing is decided for the quantity of the meal. The method of eating is advised from a viewpoint of the eating time and the amount of chewing. For example, "More slowly" and "More chewing" are presented while eating. Furthermore, any unbalanced element of the meal is counted for every weak or every month, and nourishment or calorie quantity far from the standard value is warned. When the user leaves the house without eating breakfast, a message "If you do not eat a breakfast, working efficiency in the morning falls." is presented to the user.

The sensor's "ON/OFF" is controlled by the behavior or the action in order to save electric power. For example, the acceleration sensor is set "OFF" during sleeping, and set "ON" when the user wakes up. When the user feels that the message is troublesome during the dialogue, he may voice a rejection reply such as "Shut up!" or "Stop!". If the user repeats the rejection reply, this message may not be presented to the user after confirmation (The initialization set value is changed). Instead of this message, summary of the physiological information of one day may be displayed.

Next, the wearable life support apparatus according to a second embodiment is explained. The component of the wearable terminal carried by the user is the same as the first embodiment shown in FIGS. 1 and 3. However, the physiological information and the action information are stored in a memory of main module by unit of the measurement timing. This stored information is called "sensor information corpus".

Figure 8:
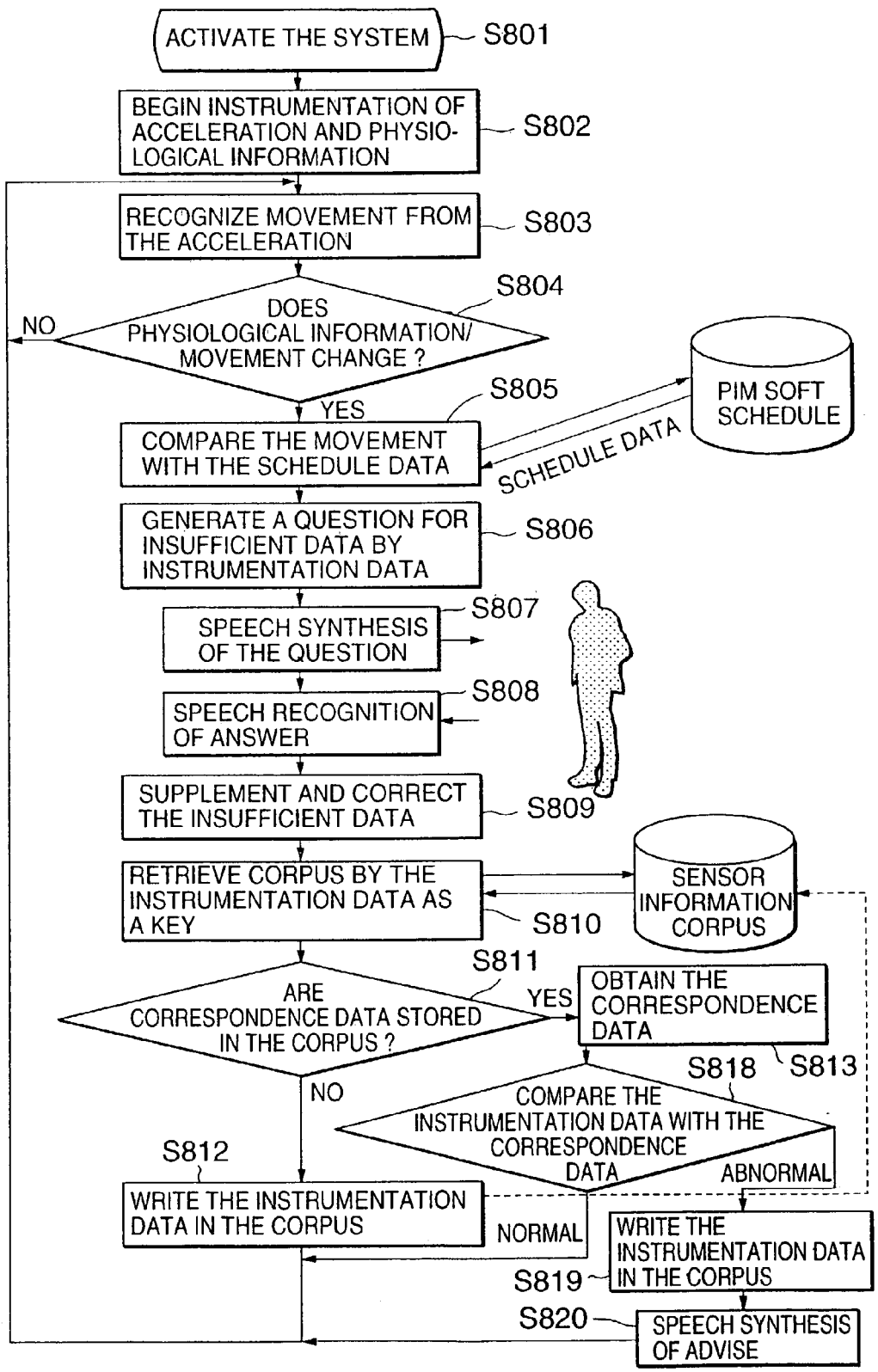
FIG. 8 is a flow chart of processing of a wearable life support apparatus according to a second embodiment.

FIG. 8 is a flow chart of processing of the system according to the second embodiment. First, the system is activated (S801), and instrumentation of the physiological information and the acceleration begins (S802). The user's posture is recognized by DC element of the acceleration, and the user's motion (periodical motion: walking, running, taking an electric train, getting in a car, riding a bicycle) is recognized by AC element of the acceleration (S803). If the instrumentation value or the action changes (S804), this action is compared with the schedule data registered in PIM soft in order to check whether it is matched with the schedule of the present time (S805). In case of non-coincidence, the schedule is confirmed by speech dialogue (S806, S807, S808). For example, a question "In the schedule, you will attend the meeting. However, are you walking in outside?" is presented to the user. When the user replies "Yes", the next question "Why do you change the schedule?" is presented to the user. When the user replies, "I have to go out because trouble occurred at a customer's office.", the system changes the schedule as "trouble at a customer's office" (S809). Next, the sensor information corpus stored in the memory of the main module is retrieved using a key such as the behavior information, the date, and the place obtained (S810).

Figure 9:
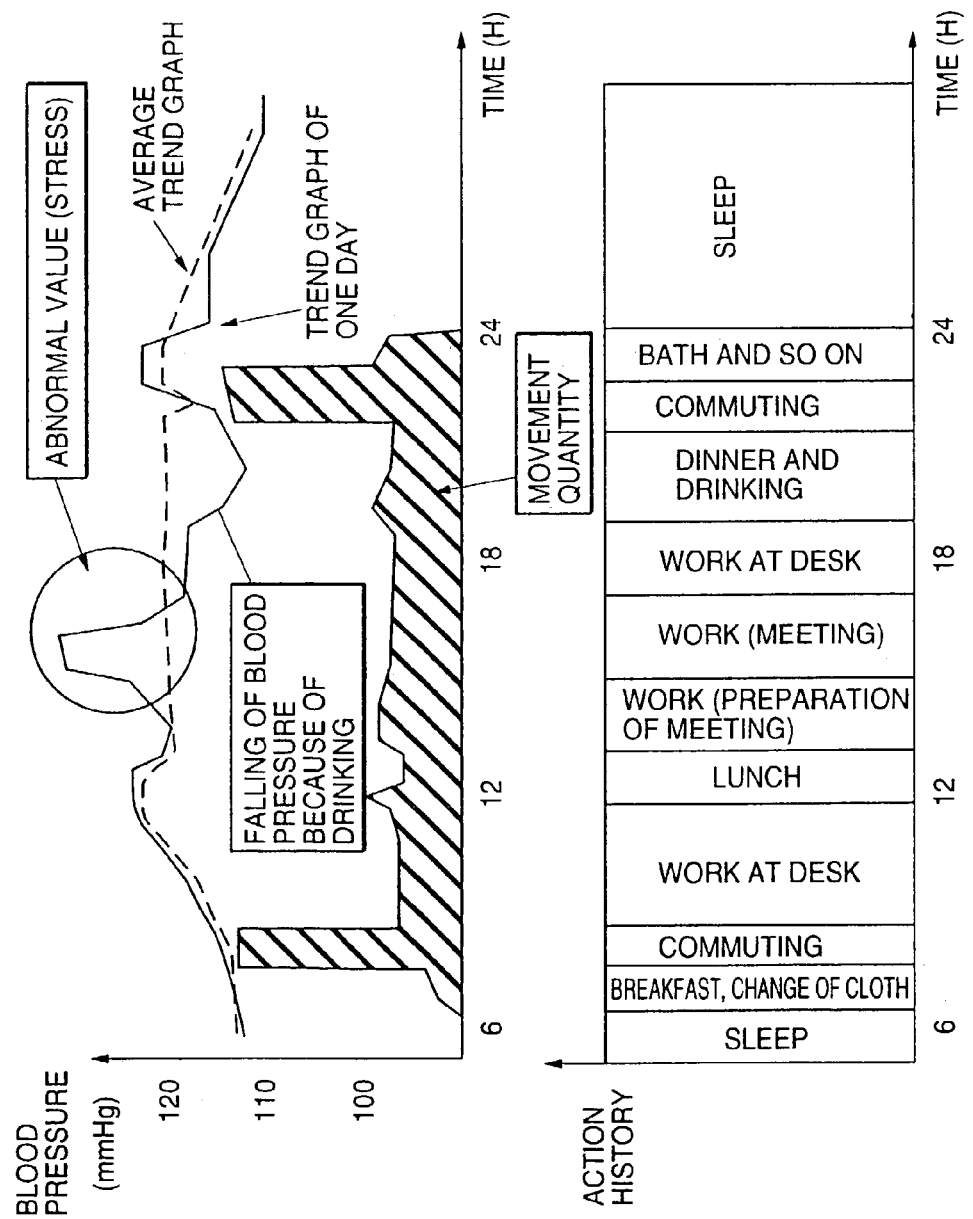
FIG. 9 is a schematic diagram of a trend graph of blood pressure during one day.

The sensor information corpus is now explained in detail. The physiological information measured by the wearable terminal is preserved in relationship with a tag such as the time, the place, the behavior, and the environment. This database is retrieved by the tag as a key and is called "sensor information corpus". The corpus represents an accumulation of data, which is used in language processing area. For example, FIG. 9 shows a trend graph representing change of the blood pressure over one day. In this way, the physiological information is mutually related with the movement quantity and the action history (commuting, work, and so on), and structured as a database. In this database, a tag representing an abnormal case or a tag representing a cause of change is recorded.

Figure 10:
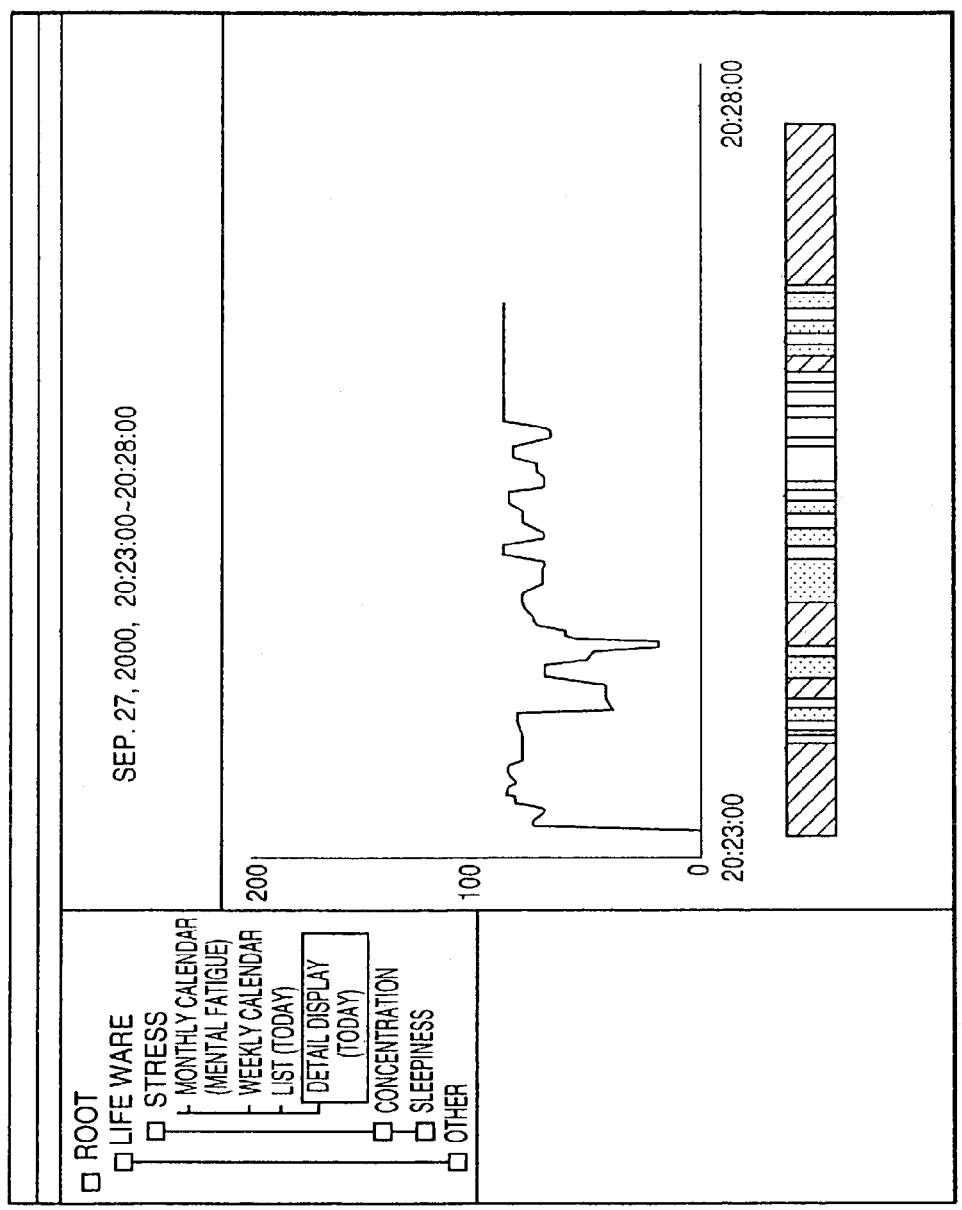
FIG. 10 is a display example of graph of pulse and action posture.
Figure 11:
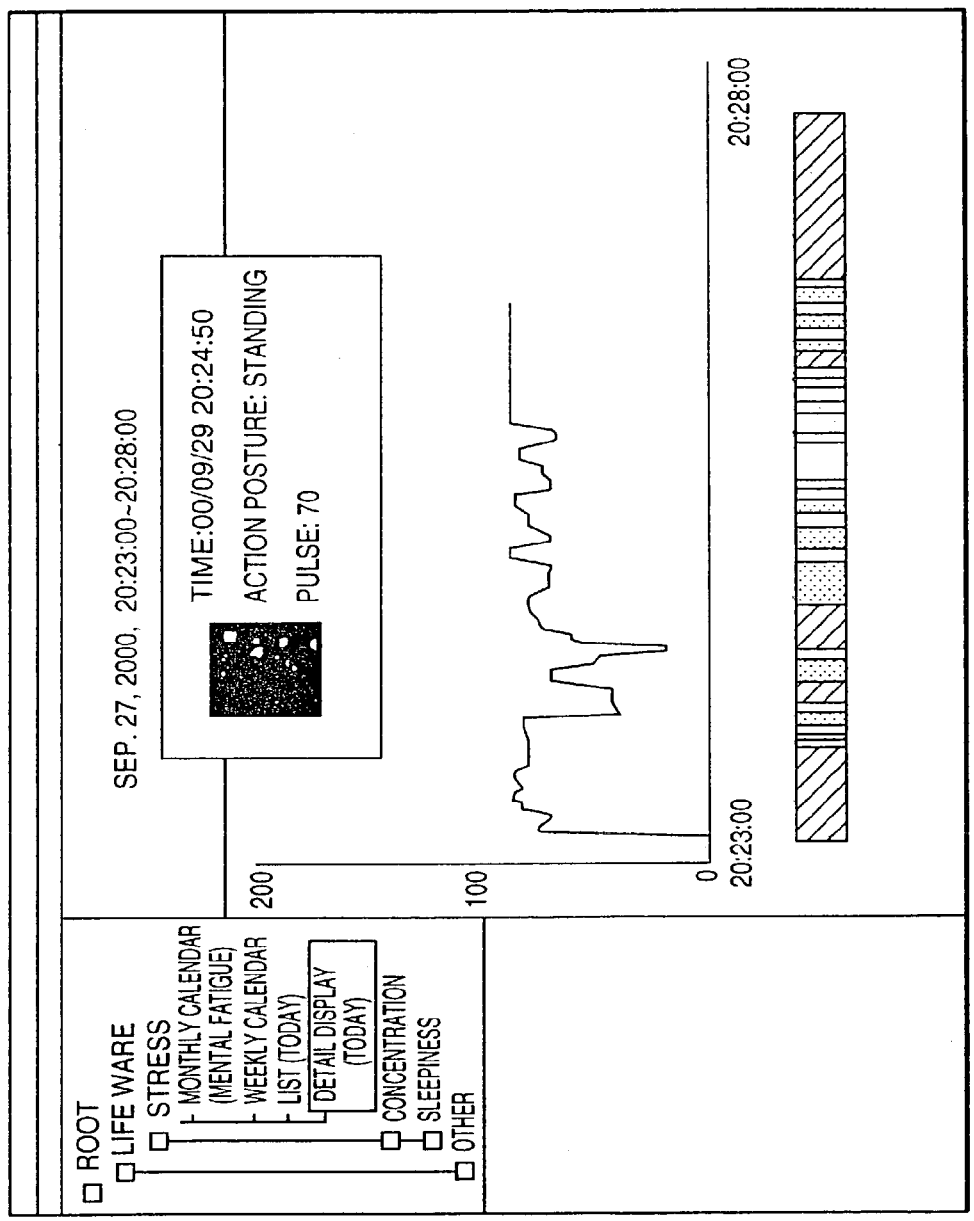
FIG. 11 is a display example of retrieval result of synchronization data with graph of pulse and action posture.

As another example, FIG. 10 is a display example of pulse change and action posture. The pulse value and the action posture of that timing are displayed by different color. When the user clicks an arbitrary point on the screen, data (time, action posture, input image, recorded speech) simultaneously collected from other sensor are retrieved from the corpus and displayed on another window as shown in FIG. 11. When the user further clicks the retrieved data on the screen, the user can refer the detail data.

Figure 12:
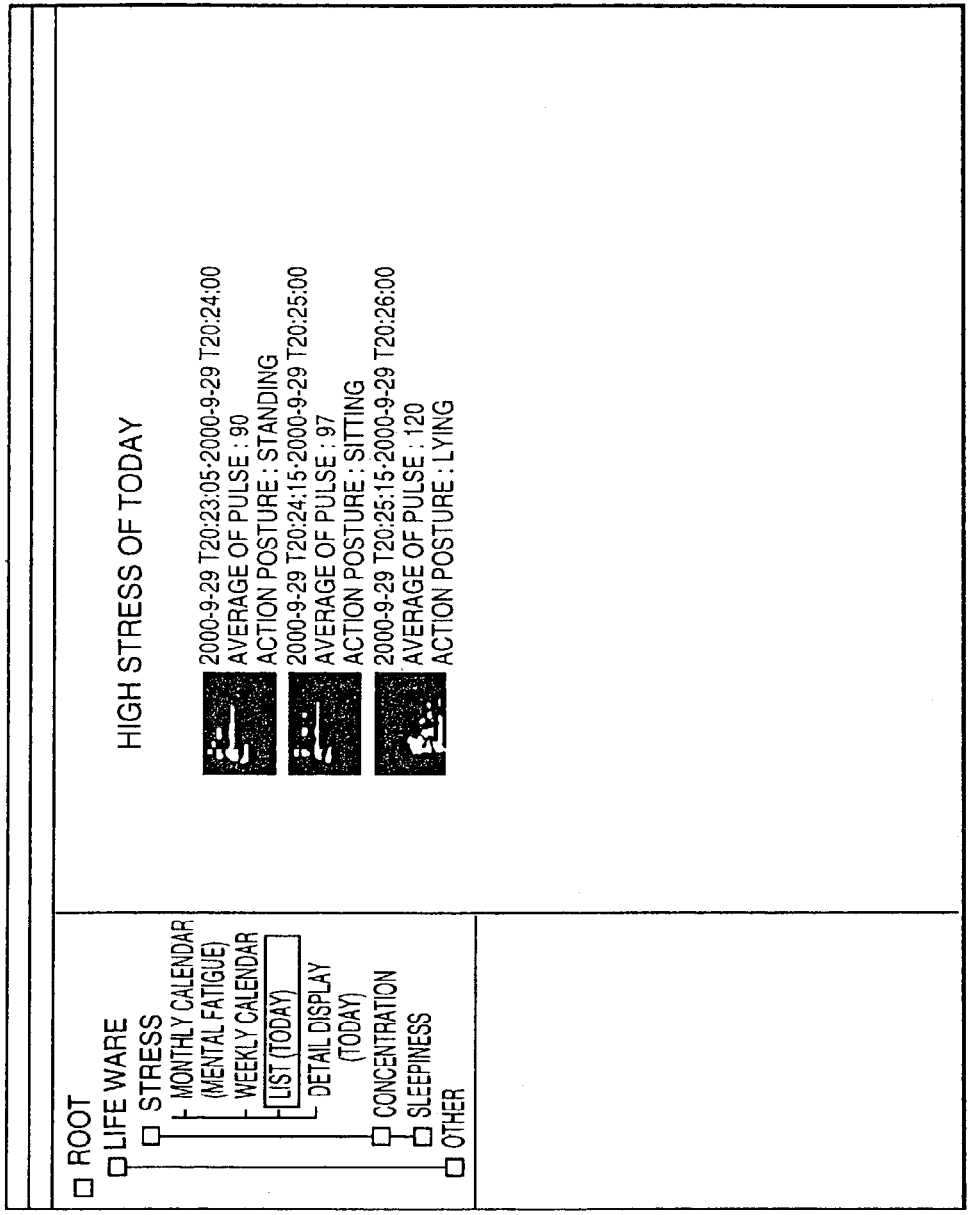
FIG. 12 is a display example of stress during one day.
Figure 13:
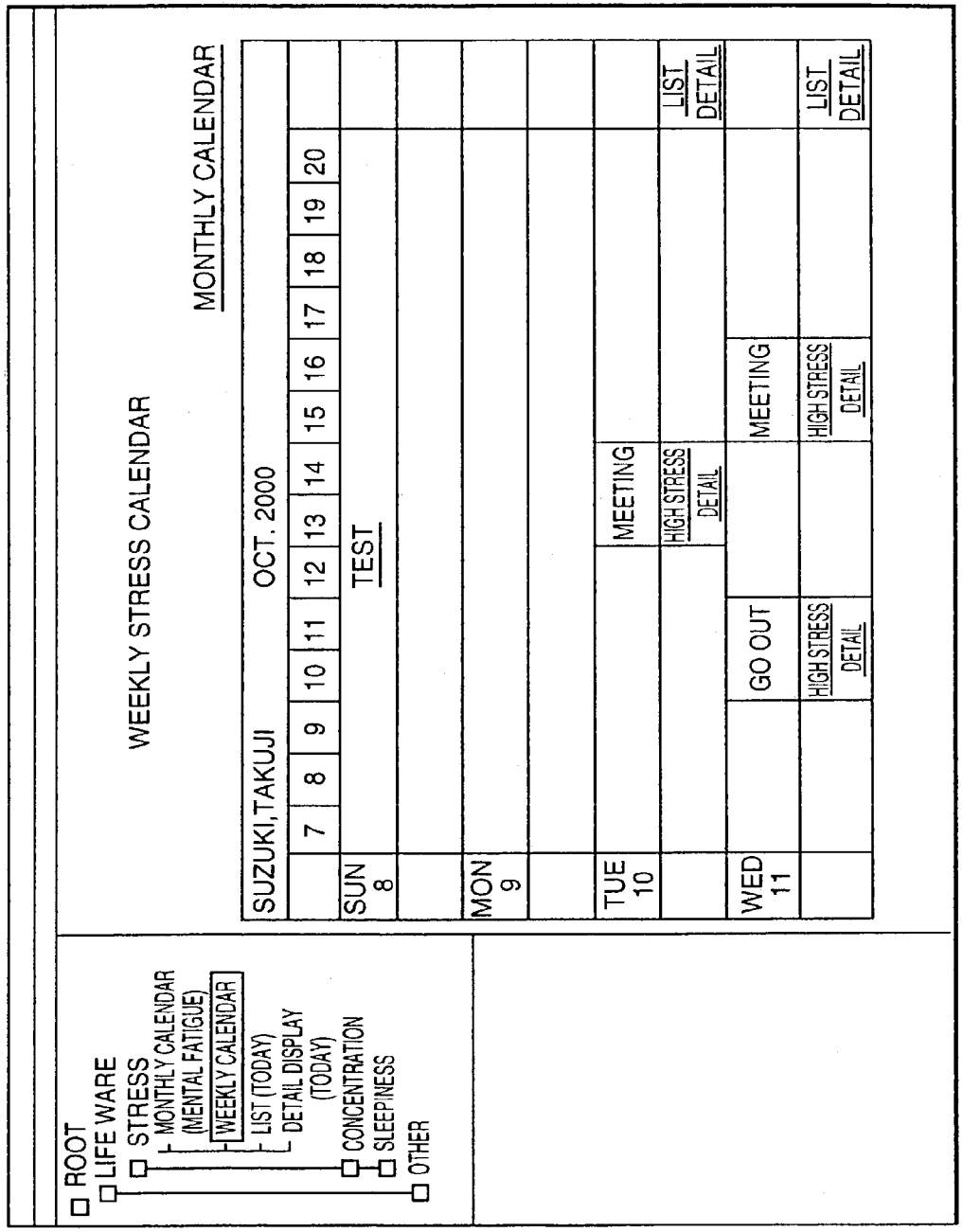
FIG. 13 is a display example of stress during one week.

Furthermore, FIGS. 12, 13 and 14 are respectively display examples of stress acquired from a plurality of physiological information during one day, one week and one month. In this way, the data can be displayed as various formats by assigning each tag.

FIGS. 15A, 15B, 15C, and 15D show examples of corpus items as four kinds of the physiological information corpus. As shown in FIG. 15A, the action content (behavior), the posture (the pitch in case of periodical movement), the pulse rate, the blood pressure, the body temperature, and the GSR values, are recorded for each date and each place. The action content represents the user's life pattern. In this case, a part of the life pattern is shown. A form of the corpus is selectively used. As shown in FIG. 15B, the average of the physiological information corpus by unit of the time or the action content is utilized as the standard. As shown in FIGS. 15C and 15D, trend corpus by sorting the trend data is utilized to display one day trend graph or one year trend graph.

Furthermore, examples of which the physiological information corpus is described by another method are shown in FIGS. 16 and 17. They are described by XML format. FIG. 16 shows description of synchronization information of each data collected by each sensor (acceleration sensor, pulse sensor, camera, microphone). FIG. 17 shows description of data from the acceleration sensor (two axes) as one example of sensor data.

In this way, when the even occurs and similar data is retrieved from the sensor information corpus (S811, S813), the measured physiological information is compared with the corpus value (the similar data) in order to decide whether the physiological information is normal (S818). In case of an abnormal result, the decision result is written in the corpus (S819), and the advice is presented to the user by speech synthesis (S820). If the similar data is not retrieved, the measured physiological information is written in the corpus (S812). As similar data to be compared with the measured physiological information, for example, the stored physiological information of the same time before one week for the same behavior is retrieved from the corpus. This comparison object is changed in the set mode mentioned in the first embodiment. For example, if the average value of one month, or the stored physiological information of the same period in last year is indicated, the comparison result is replied. When the measured physiological information as the comparison object is decided to be abnormal, this physiological information is newly stored in the corpus. Furthermore, when the user activates his carrying display (104, 304), the display outputs the trend graph of one week or one month in the past. Alternatively, when the alarm is previously output to the user, the user may activate the display to output the trend graph.

As the registration to the corpus, all data when the action information or the physiological information changes can be acquired. However, some physiological information is periodically measured (For example, at thirty minute intervals). If the all trend data of one day includes a problem, the problem is registered as the tag. Furthermore, these data may be registered as a personal database in relation with the life pattern (action history).

Furthermore, if the user executes action/behavior as a cause of which the physiological information changes, the physiological information is changing by the action/behavior along time. However, the time on which the change appears is different by the kind of the physiological information. Accordingly, when the action/behavior as the cause of which the physiological information changes occurs, the change of the physiological information is measured after passing the time predetermined by the kind of the physiological information, and the instrumentation data are recorded in the corpus in relation to the action/behavior. For example, weight change in case of having a meal is measured just after the meal. However, glucose level is measured after thirty minutes from the meal and recorded in the corpus in relation to the meal (If necessary, content of the meal). Alternatively, the instrumentation may be continuously executed. In case of data retrieval, the retrieval area may be called from a table by the kind of the physiological information. For example, the instrumentation period of the glucose level is set as one hour in the table. If the user selects the meal (For example, breakfast) in the action through the action graph screen, "one hour" is read from the table and a graph of glucose level during one hour after the meal is displayed. Furthermore, if a graph of electrocardiogram is set as one graph, only one graph is extracted by clicking one point on displayed graph.

Furthermore, above-mentioned similar data retrieval can be executed by real time. When the similar data is retrieved from the sensor information corpus by real time using the physiological information/action information measured by the sensor module 102 (302), the similar data may be simultaneously output through the display 104 (304) and the status may be reappeared in order for the user to recognize the present status. For example, in case that the pulse as the physiological information and the action/posture information from the acceleration sensor as the behavior information are recorded, and the dynamic image and the speech are simultaneously recorded, if the instrumentation data is abnormal based on the change of pulse and the behavior information in comparison with the past average value, the past data similar to the change pattern is retrieved. In addition to the pulse rate data (or graph) and the behavior information of the present status, the dynamic image and the speech in the retrieved data are output through the display 104 (304).

Furthermore, the trend data in case of normal results is averaged by unit of one day, one week, one month, one year for the same life pattern (the same action), and processed as the average trend data.

Figure 19:
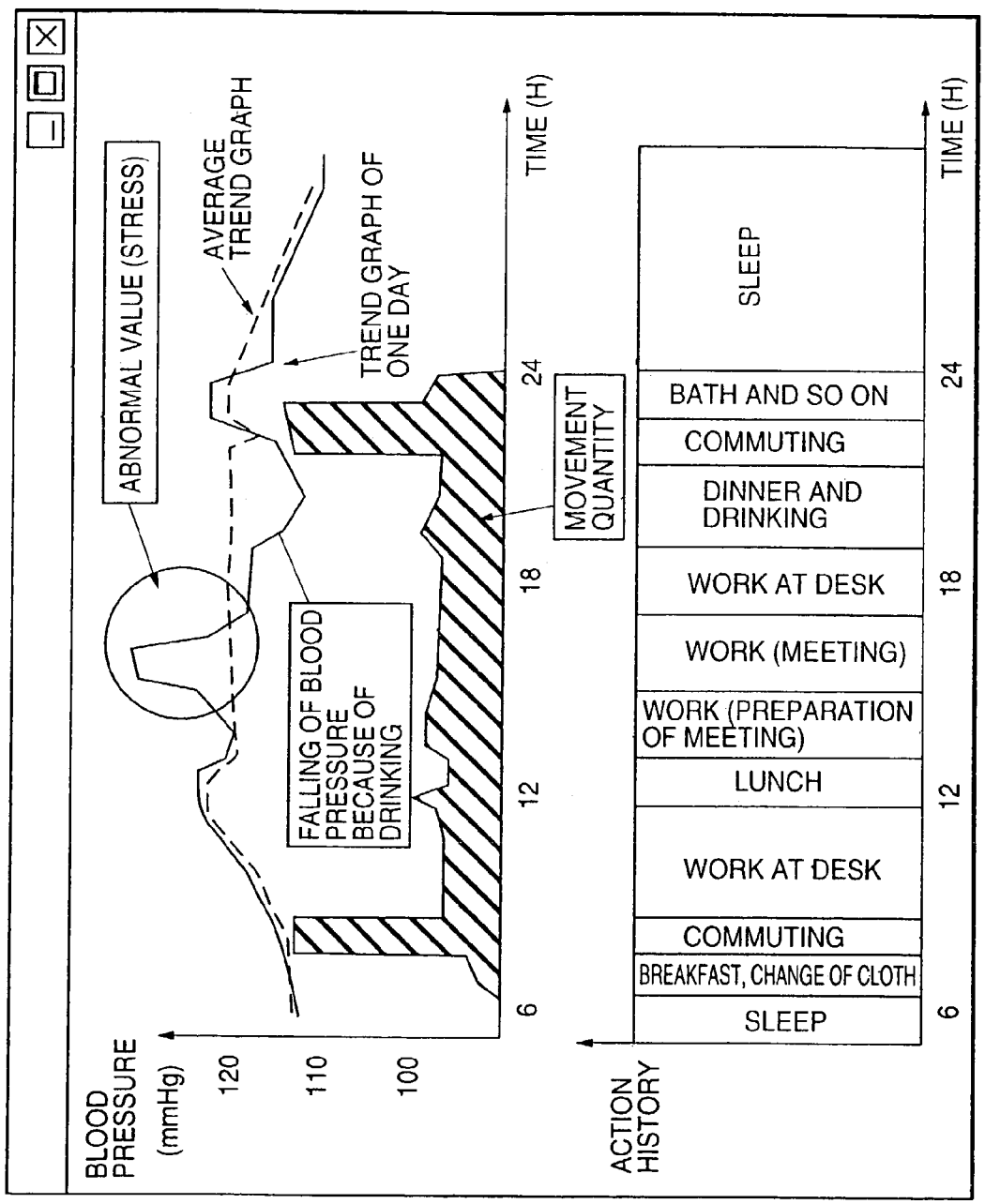
FIG. 19 is an example trend graph of blood pressure during one day shown on the portable display.

As mentioned-above, when the user thinks that the message is troublesome, he voices a rejection message such as "Shut up!" or "Stop!". If the user repeatedly utters the rejection message, the system does not present the advice after confirming with the user. This user's indication is preserved in the corpus, and summed up at the end of each month. The fact that the threshold is loosely reset may be presented to the user in order for the user to reconsider. Furthermore, when the present time coincides with a preset time (For example, 10:00 PM, or after dinner), the average value of the physiological information (the blood pressure, the pulse, the body temperature, GSR) of one day is calculated for each behavior, and presented by speech message. If the user is interested in this message, he indicates the behavior to display the detail information. In response to the indication, the detail information (FIG. 18) or the trend graph (FIG. 19) related with the indicated behavior is presented through a portable display or a home television. As the presentation method, the average value of one day of each behavior is displayed as a list, and the trend graph of one week and one month in the past is also displayed in case of indication. Furthermore, the number of footsteps is calculated from the pulse value and the acceleration data, and calorie consumption is calculated from the number of footsteps and the behavior information. The calorie of one day is decided by the consumption calorie and absorbed calorie of all meals. Then, a warning that the user suffers a lack of exercise, the user had too much food, or the nourishment is biased is output to the user.

A method of measuring the stress degree using the pulse or GSR is explained. In case of the pulse, when the measured pulse is faster than a preset limit or normal value, it is confirmed whether the user is moving from just before (several tens of seconds before) by the AC element of the acceleration sensor. If the user is not moving, the abnormal status of the pulse is decided to be caused by a psychological change of the user, and a product of the pulse rate is calculated as the stress degree. In case of GSR, if a first transition of change is faster than the preset timing, the first transition is counted up as the stress degree. The counted value is displayed at a predetermined time (For example, before sleeping), and the comment is additionally displayed. For example, if the counted value is within the limit being under stress, the comment "Today, you are under stress. Please relax by listening to music or taking a tepid bath slowly." is displayed. Furthermore, at the end of each week, a weekly summary of the health condition may be displayed. The user can indicate the display of the summary if necessary.

Figure 20:
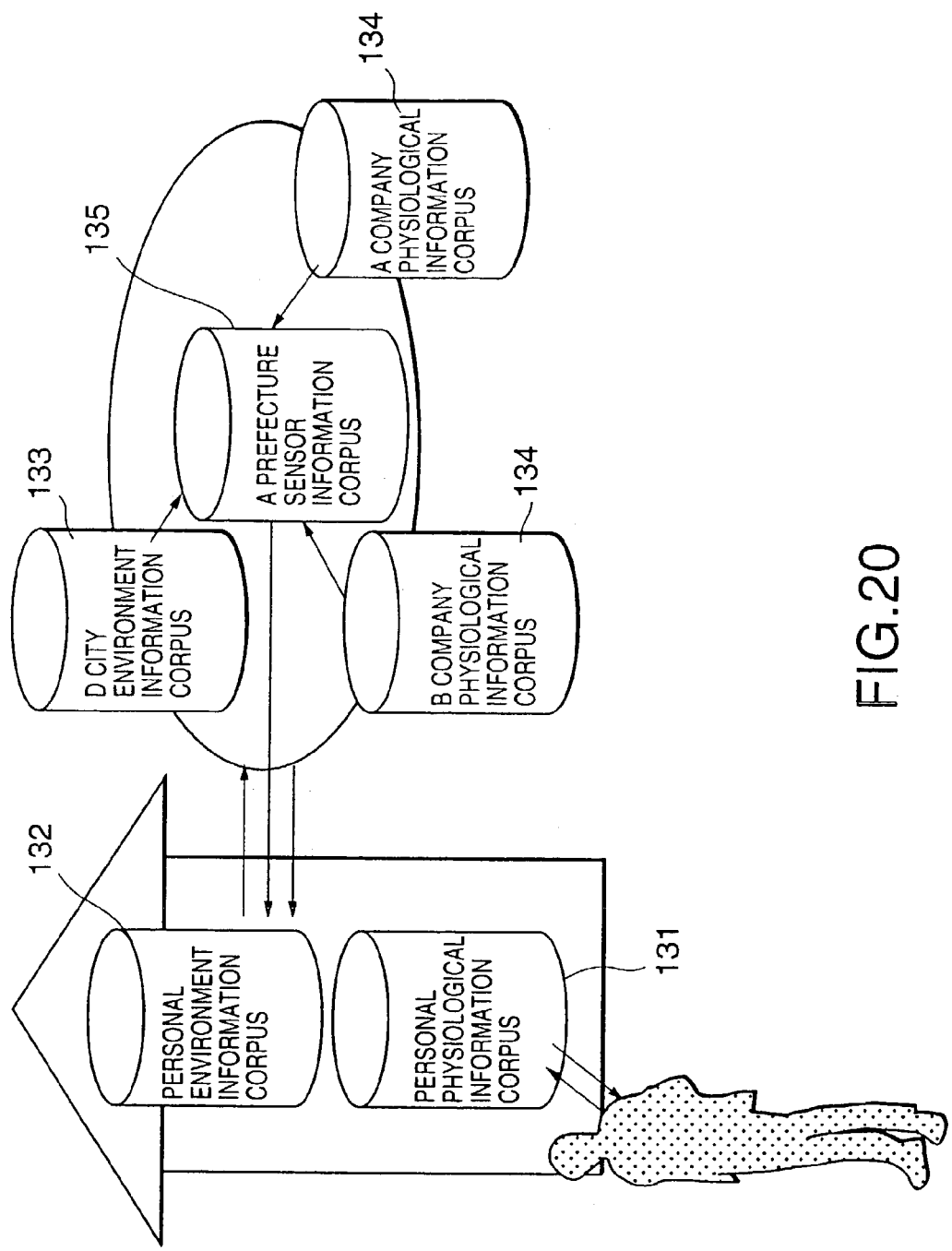
FIG. 20 is a block diagram of a wearable life support system including personal corpuses and sensor information corpus on an outside network according to a third embodiment.

Next, the wearable life support apparatus according to a third embodiment is explained. The component of the wearable terminal carried by the user is the same as the first embodiment (FIG. 1 or FIG. 3). However, in the outside, a home server stores the physiological information, the action information, and the environment information acquired from an outside network, and an area server manages the information in an ambient area. The system of the third embodiment includes the home server and the area server. FIG. 20 is a block diagram of the wearable life support system according to the third embodiment. As shown in FIG. 20, the home server includes a personal physiological information corpus 131 and a personal environment information corpus 132 that stores environment information surrounding the user. The area server includes a city environment information corpus 133 that stores local environment information of city, town, village, and a company physiological information corpus 134 that stores information for each area or each company. These corpora are mutually connected by a network. The city environment information corpus 133 and the company physiological information corpus 134 may be merged as a prefecture or state sensor information corpus 135.

Figure 21:
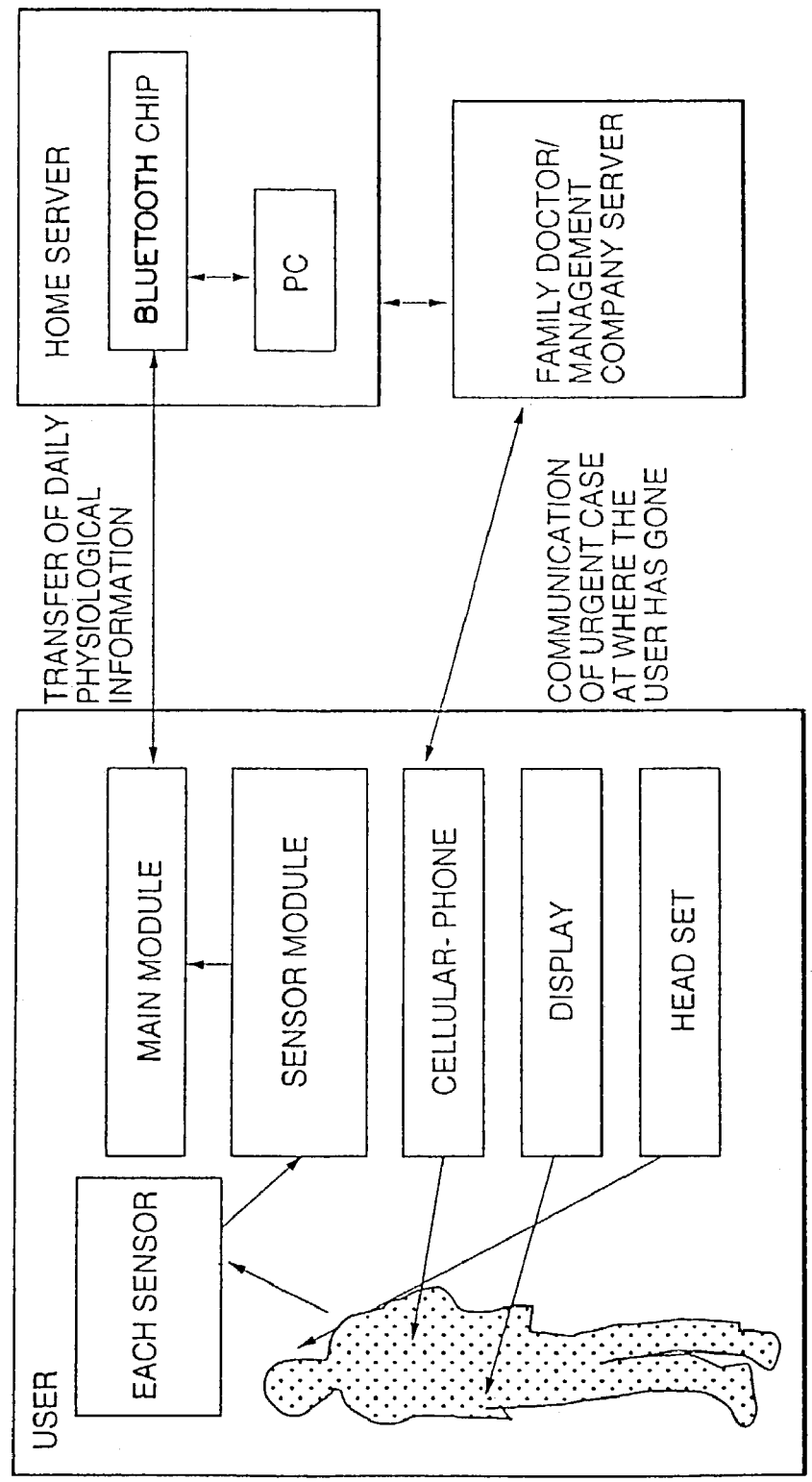
FIG. 21 is a block diagram showing a relationship among the wearable terminal, a home server, and a family doctor/management company server according to the third embodiment.

Next, FIG. 21 is a block diagram showing a relationship among the wearable terminal, the home server, and a family doctor/management company server according to the third embodiment. As shown in FIG. 21, the physiological information and the action information measured by the wearable terminal are stored in a memory of the wearable terminal, and transferred to the home server. The home server retrieves the personal environment information corpus 132 and the prefecture sensor information corpus 135 of local/company server based on the transferred information and obtains the environment information (temperature, humidity, and so on) surrounding the user and the user's status information such as place or the user's facing person through the network. In short, the data set similar to the user's present status is retrieved from the information and downloaded to the wearable terminal. Alternatively, the corpus data related to the user's status is previously downloaded from the server to the wearable terminal. However, in an unexpected case, the wearable terminal obtains the relationship data through communication by accessing the home server or a public server. For example, in case the user is a salaried man of business job, the user's status information represents personal data of the salaried man of business job and personal data of a person of similar environment stored in the sensor information corpus of outside.

In the sensor information corpus of the third embodiment, in addition to the physiological information and the action information of the second embodiment, the environment information such as temperature, humidity, the image of the user's facing person, and speech surrounding the user are stored. These data are transferred to the home server through the cellular-phone at a predetermined time, or are directly transferred to the home server by Bluetooth when the user is at home. In this case, the sum result and the stress degree of one day, and the trend data are displayed using the home server.

The wearable life support system is connected to an outside network. Accordingly, the following use situations are considered. As the use situation in life scene, in case of excretion, the status that the user enters a toilet room is detected by location recognition using a wireless tag or by speech dialogue during the user's walking in the house. In this case, a weighing machine and a body fat machine respectively detects the user's weight and body fat. The component of excretions is analyzed and transferred to the main module of the wearable terminal through Bluetooth.

It is difficult for the user to wear the wearable sensor while the user is taking a bath. Accordingly, an electrocardiogram sensor set to the bath detects the user's heart rate. After taking a bath, when the user wears the wearable terminal again, these data are transferred from the memory of the bath to the wearable terminal through Bluetooth.

Furthermore, an electrode to recognize the body wear is equipped in the wearable terminal. By detecting whether the electrode is exciting or insulating, the status whether the user wears the wearable terminal is recognized. While the user interacts speech dialogue through the wearable terminal or wears the display of the wearable terminal, the information is presented to the user by using these devices. While the user takes off the wearable terminal, the interface is exchanged to the dialogue system or the information system (For example, a home information terminal) surrounding the user. In short, the presentation means including the surrounding interface is exchanged by detachability of the wearable terminal.

In the above-mentioned three embodiments, the information presentation to the user is executed by the speech synthesis. However, this presentation may be executed by image or character through a head-mounted display, a pendant type display, or a wristwatch type display. Furthermore, if a message for the user is stored, a vibrator is built in the wristwatch type display or the cellular-phone and the existence of the message is informed to the user by the vibrator.

Furthermore, the feedback media for the user's status is changed based on the measured/recognized behavior. For example, speech is utilized while walking, and the display is utilized while working. The message is not presented while sleeping. In case of an urgent status, this information is sent to those around the user, a family doctor, or a management company in addition to the user. When a serious case (the user himself can not cope with) is detected, this status is broadcast to a plurality of terminals of those around the user. In this case, the media is converted according to the use mode of each terminal in order to inform who and where the serious status occurs. By adding the urgent degree, for example, the more urgent status is informed by the larger volume.

If it is necessary that the user must measure the physiological information by oneself (if automatic instruction and data transmission can not be executed), a message to urge the user to measure is displayed according to the instrumentation schedule. If the user does not measure the physiological information, a message to force the instrumentation is periodically displayed (The method for displaying the message is interactively controlled.).

Another use situation using the above-mentioned component is explained. When the wearable terminal downloads prescription data of the doctor from a hospital server, a message to urge the user to prescribe medicine based on the data is displayed in cooperation with the user's behavior. For example, after having a meal, by displaying a message "Please take two capsules of medicine after a meal.", the user's taking is confirmed and preserved as the record. An electrical signature is assigned to the prescription data in order to clear the doctor's responsibility. Personal information such as the condition of a patient or the case history is additionally preserved. In case of an urgent case, those around the patient, ambulance operators, and the doctor can refer the personal information.

Furthermore, a route guidance based on the user's status can be presented. The route guidance represents a service to present a course from the user's present location (or the nearest station) to the destination. In case of determining the course, the physiological information and the action information acquired by the wearable sensor are additionally used as parameters (constraint conditions). For example, if the user's fatigue degree is high, a route for the user to follow without stairs is created. The fatigue degree is extracted by the condition such as the case that the user exercised greatly or the user repeatedly executed the same working while the behavior information is continuously measured. In this case, a question "Are you tired?" is presented to the user. The parameter of the fatigue degree is slightly controlled by this result.

In the third embodiment, Bluetooth is used as the communication between the modules. However, if the communication of personal level is executed, various kinds of methods are selectively utilized. The special technique (PAN: Personal Area Network) to process electric signal by using the human body as a conductor may be utilized. In the same way, IrDA may be utilized. The above-mentioned three embodiments are explained by the wireless communication. However, the wired communication such as RS232C may also be used.

Figure 22:
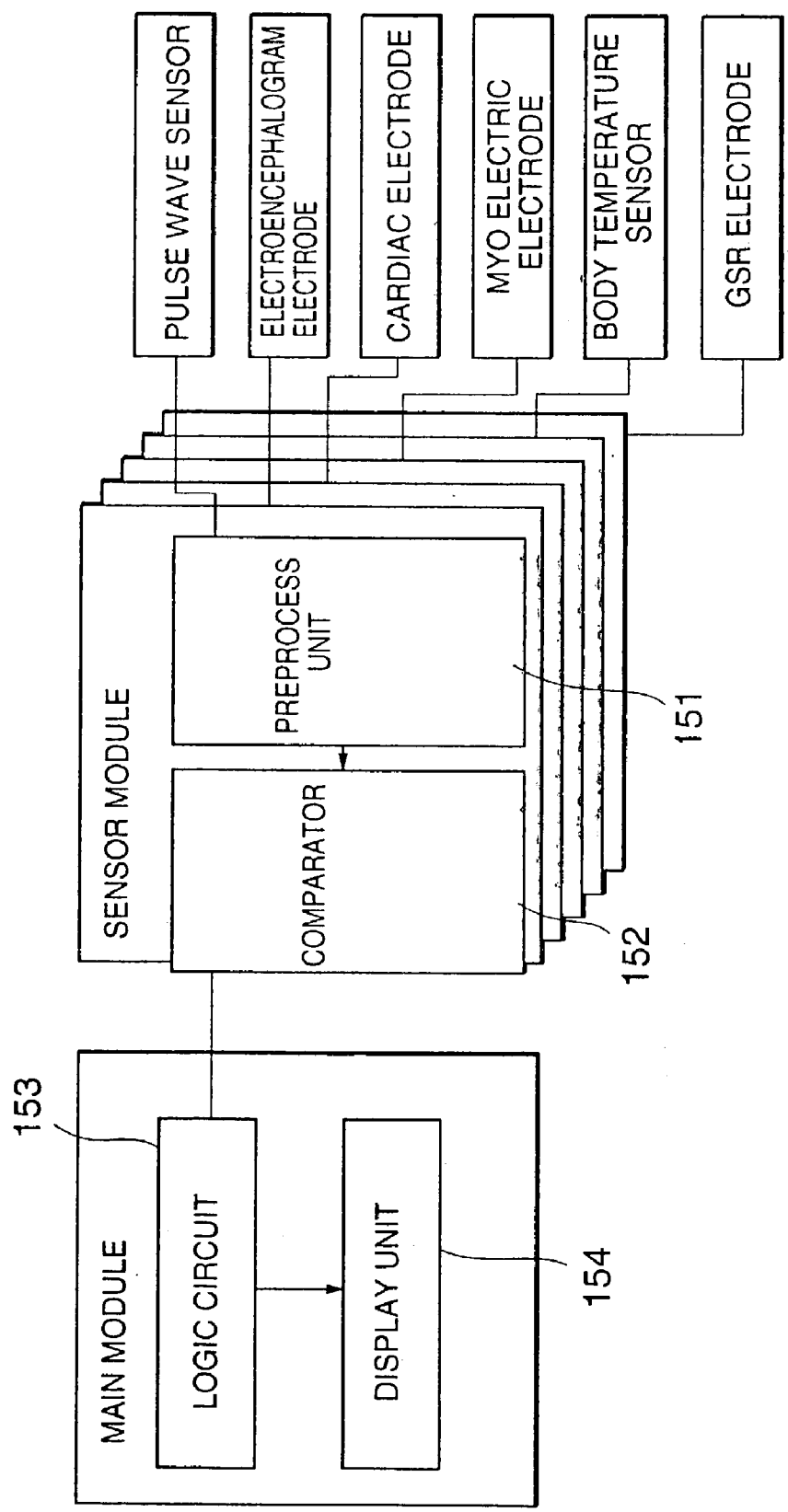
FIG. 22 is an example of components of a sensor module of the wearable life support apparatus using analogue circuits.

In the third embodiment, the instrumentation data is processed by A/D conversion, and the user's status is decided by using a digital signal. However, it may be decided by analogue signal processing. FIG. 22 shows an example of component of the sensor module using the analogue circuit. As shown in FIG. 22, after analogue signals from each sensor pass through a preprocess unit 151, a comparator 152 processes the signals by the threshold and outputs digital signals "0" "1" as the status information. A logic circuit 153 detects the user's status by referring to the digital signals, and the detection result is output through a display unit 154 (LED, LCD, and so on).

Next, modification examples of above-mentioned embodiment are explained. The component of the wearable terminal carried by the user is the same as the first embodiment. In this case, a method for retrieving the similar data from the sensor information corpus and for displaying as waveform level is explained. FIG. 23 shows one example of graph of the physiological information measured by the wearable terminal. If this waveform includes a part of which the user wishes to refer similar instances in the past, the user indicates the part as a square area (or ellipse and so on) using area indication means (For example, mouse or pen) as shown in FIG. 24. The indicated area is regarded as retrieval request data and a part similar to the waveform in the indicated area is retrieved by pattern matching. Furthermore, if a characteristic event is included in adjacent data of the similar part, the event is additionally displayed. FIG. 25 is one example of the retrieval result. In this way, the user can previously know some fit and receive a suitable treatment early.

Furthermore, in this case, the retrieval method or the recognition method may be controlled by the indicated shape of the area. For example, as for the area surrounded by the square, similar one is retrieved from the past data. As for the area surrounded by the ellipse, it is simply decided whether the data in the area is normal or abnormal. In case of abnormal, even if the shape is not similar, the past data in case of abnormal can be displayed.

Figure 26:
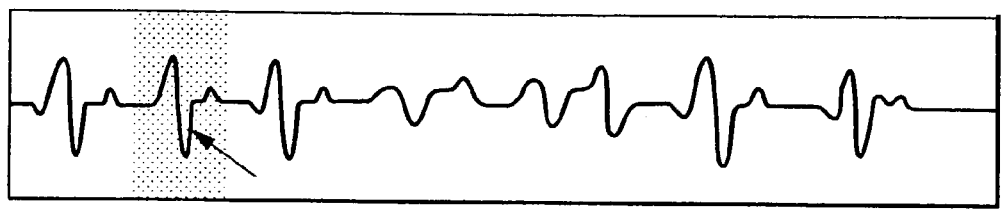
FIG. 26 is a selection example of one pulse of electrocardiogram graph.
Figure 27:
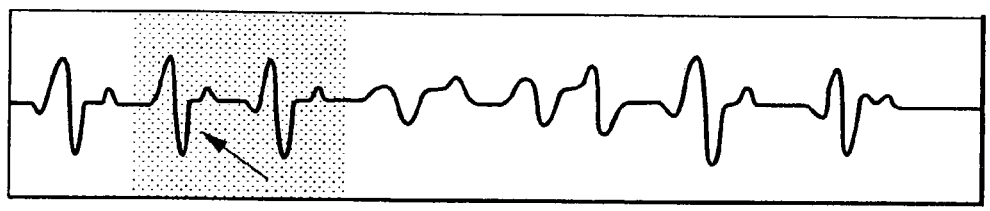
FIG. 27 is a selection example of two pulses of electrocardiogram graph.

Furthermore, in case of periodical physiological information such as electrocardiogram, the area can be indicated by the number of operation times using the area indication means except for above-mentioned area indication. For example, when the user operates a mouse as the area indication means, in case of single click as shown in FIG. 26, the waveform of one pulse is selected for retrieval. In case of double clicks as shown in FIG. 27, the waveform of two pulses are selected for retrieval.

Figure 28:
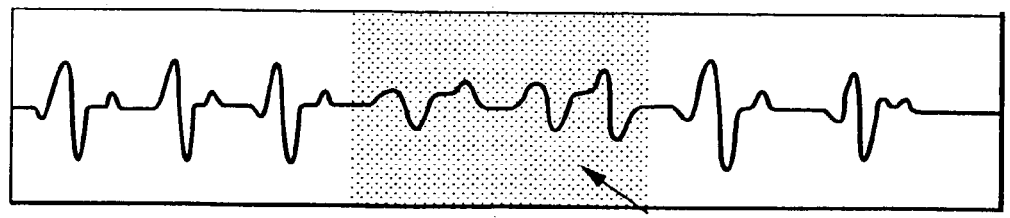
FIG. 28 is a selection example of arrhythmia of electrocardiogram graph.

Furthermore, abnormal detection means for recognizing/detecting some abnormal part in the physiological information may be prepared. For example, in case of electrocardiogram, arrhythmia data is automatically detected. In response to the click operation, all of abnormal data can be selected and retrieved as shown in FIG. 28. In this case, the abnormal detection means may relatively detect the abnormal part by comparing with the past average value in the sensor information corpus. Otherwise, the abnormal detection means may absolutely detect the abnormal part by medical knowledge.

Furthermore, above-mentioned similar data retrieval can be executed by real time. When the similar data is retrieved from the sensor information corpus by real time using the physiological information/action information measured by the sensor module 102 (302), the similar data may be simultaneously output through the display 104 and the status may be reappeared in order for the user to recognize the present status. For example, in case that the pulse as the physiological information and the action/posture information from the acceleration sensor as the behavior information are recorded, and the dynamic image and the speech are simultaneously recorded, if the instrumentation data is abnormal based on the change of pulse and the behavior information in comparison with the past average value, the past data similar to the change pattern is retrieved. In addition to the pulse value (or graph) and the behavior information of the present status, the dynamic image and the speech in the retrieved data are output through the display 104 (304).

As mentioned-above, in the wearable life support apparatus of the present invention, the physiological information and the action information are correspondingly measured from the user's body. Accordingly, the user's health condition is decided by the physiological information related with the action, and adequate advice is presented to the user. Furthermore, by comparing the action information with the user's schedule, the user's life custom is correctly guided to the user's desired schedule.

A memory device, such as a CD-ROM, floppy disk, hard disk magnetic tape, or semiconductor memory can be used to store instructions for causing a processor or computer to perform the processes described above.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A wearable device, comprising
   a main module configured to include a wireless communication chip and a memory, the memory storing a schedule of a user and a table representing a correspondence between each action information and each behavior of the user;
   at least one sensor module configured to include a wireless communication chip;
   at least one sensor configured to be coupled to said at least one sensor module, to acquire action information of the user; and
   a display configured to include a wireless communication chip;
   wherein said main module retrieves a behavior corresponding to the action information from the table, compares the behavior with the schedule, and, when the behavior does not match with the schedule, outputs a non-coincidence message between the behavior and the schedule through said display.

2. The wearable device according to claim 1,
   wherein a plurality of sensors are coupled to said at least one sensor module.

3. The wearable device according to claim 1,
   wherein each of a plurality of sensors is differently coupled to one of a plurality of sensor modules.

4. The wearable device according to claim 1,
   wherein when the action information is continually acquired while the action information changes, said main module decides whether the behavior corresponding to the action information matches with the schedule.

5. The wearable device according to claim 4,
   wherein said sensor module executes preprocessing of a signal from the sensor, and transmits a preprocessed signal to said main module through the wireless communication chip.

6. The wearable device according to claim 5,
   wherein said main module analyzes the preprocessed signal, and transmits analysis information to said display through the wireless communication chip.

7. The wearable device according to claim 6,
   wherein said display outputs the analysis information, and
   wherein the microphone inputs reply information from the user, and transmits the reply information to said main module through the wireless communication chip.

8. The wearable device according to claim 7,
   wherein said main module corrects the analysis information by using the reply information, and stores corrected analysis information.

9. The wearable device according to claim 1,
   further comprising a head set being configured to include a wireless communication chip, a camera, and a microphone.

10. The wearable device according to claim 1,
    wherein when a microphone inputs supplemental information representing a reason for the non-coincidence from the user, said main module corrects the schedule by referring to the supplemental information.

11. A wearable device, comprising:
    a main module configured to include a wireless communication chip and a memory, the memory storing a schedule of a user and a table representing a correspondence between each action information and each behavior of the user;
    at least one sensor module configured to include a wireless communication chip;
    at least one sensor configured to be coupled to said at least one sensor module, and to acquire action information of the user; and
    a cellular phone configured to include a wireless communication chip,
    wherein said main module retrieves a behavior corresponding to the action information from the table, compares the behavior with the schedule, and, when the behavior does not match with the schedule, outputs a non-coincidence message between the behavior and the schedule through said cellular phone.

12. The wearable device according to claim 11, further comprising a head set configured to include a wireless communication chip, a camera, and a microphone.

13. The wearable device according to claim 11, wherein when the action information is continually acquired while the action information changes, said main module decides whether the behavior corresponding to the action information matches with the schedule.

14. The wearable device according to claim 11, wherein when said cellular phone inputs supplemental information representing a reason for the non-coincidence from the user, said main module corrects the schedule by referring to the supplemental information.

15. The wearable device according to claim 11, wherein a plurality of sensors are coupled to said at least one sensor module.

16. The wearable device according to claim 11, wherein each of a plurality of sensors is differently coupled to one of a plurality of sensor modules.

17. The wearable device according to claim 11, wherein said sensor module executes preprocessing of a signal from the sensor, and transmits a preprocessed signal to said main module through the wireless communication chip.

18. The wearable device according to claim 17, wherein said main module analyzes the preprocessed signal, and transmits analysis information to said cellular phone through the wireless communication chip.

19. The wearable device according to claim 18, wherein said cellular phone outputs the analysis information to a user, inputs reply information from the user, and transmits the reply information to said main module through the wireless communication chip.

20. The wearable device according to claim 19, wherein said main module corrects the analysis information by using the reply information, and stores corrected analysis information.

* * * * *